US012543775B2

(12) United States Patent
Lang et al.

(10) Patent No.: US 12,543,775 B2
(45) Date of Patent: Feb. 10, 2026

(54) METHODS FOR REDUCING ONE OR MORE TOBACCO SPECIFIC NITROSAMINES IN TOBACCO MATERIAL

(71) Applicant: PHILIP MORRIS PRODUCTS S.A., Neuchatel (CH)

(72) Inventors: Gerhard Lang, Murten (CH); Irfan Gunduz, Le Mont-sur-Lausanne (CH); Aline Vuarnoz-Bize, Onens (CH)

(73) Assignee: Philip Morris Products S.A., Neuchatel (CH)

( * ) Notice: Subject to any disclaimer, the term of this patent is extended or adjusted under 35 U.S.C. 154(b) by 86 days.

(21) Appl. No.: 14/775,910

(22) PCT Filed: Mar. 14, 2014

(86) PCT No.: PCT/EP2014/055209
§ 371 (c)(1),
(2) Date: Sep. 14, 2015

(87) PCT Pub. No.: WO2014/140346
PCT Pub. Date: Sep. 18, 2014

(65) Prior Publication Data

US 2016/0029689 A1 Feb. 4, 2016

(30) Foreign Application Priority Data

Mar. 15, 2013 (EP) .................................... 13159620

(51) Int. Cl.
*A24B 15/24* (2006.01)
*A24B 15/12* (2006.01)
*G01N 33/483* (2006.01)

(52) U.S. Cl.
CPC ............ *A24B 15/245* (2013.01); *A24B 15/12* (2013.01); *G01N 33/4833* (2013.01)

(58) Field of Classification Search
None
See application file for complete search history.

(56) References Cited

U.S. PATENT DOCUMENTS 3,353,541 A 11/1967 Hind
3,386,449 A 6/1968 Hind
(Continued)

FOREIGN PATENT DOCUMENTS

CN 1477935 A 2/2004
EP 1623634 2/2006
(Continued)

OTHER PUBLICATIONS

Office Action issued in China for Application No. 201480014073.4 dated Feb. 13, 2017 (19 pages). English translation included.
(Continued)

*Primary Examiner* — Phu H Nguyen
(74) *Attorney, Agent, or Firm* — Mueting Raasch Group

(57) ABSTRACT

There is described herein a method of reducing the amount of at least matrix-bound NNK in tobacco material comprising the steps of: (a) providing tobacco material comprising at least matrix-bound NNK; (b) optionally measuring the level of at least matrix-bound NNK in the tobacco material; (c) heating the tobacco material for at least about 30 seconds to a temperature of greater than about 110 degrees Celsius in the presence of a liquid or steam to release at least a portion of the matrix-bound NNK from the insoluble tobacco matrix of the tobacco material; (d) optionally measuring the level of at least matrix-bound NNK in the tobacco material following step (c); (e) optionally comparing the levels of matrix-bound NNK obtained in steps (b) and (d); and (f) identifying tobacco material in which at least matrix-bound NNK has been removed from the tobacco material.

13 Claims, 5 Drawing Sheets

(56) References Cited

U.S. PATENT DOCUMENTS

| | | | | | |
|---|---|---|---|---|---|
| 3,415,253 | A | | 12/1968 | Michels | |
| 3,420,241 | A | | 1/1969 | Hind | |
| 3,428,053 | A | | 2/1969 | Schoenbaum | |
| 3,467,109 | A | | 9/1969 | Block | |
| 3,483,874 | A | | 12/1969 | Bickenheuser, Jr. | |
| 3,561,451 | A | | 2/1971 | Jacin | |
| 3,760,815 | A | | 9/1973 | Deszyck | |
| 3,847,164 | A | | 11/1974 | Mattina | |
| 3,860,012 | A | | 1/1975 | Selke | |
| 4,182,349 | A | | 1/1980 | Selke | |
| 4,341,228 | A | | 7/1982 | Keritsis | |
| 4,674,519 | A | | 6/1987 | Keritsis | |
| 5,060,669 | A | * | 10/1991 | White | A24B 15/24 131/297 |
| 5,445,169 | A | | 8/1995 | Brinkley | |
| 5,584,306 | A | | 12/1996 | Beauman | |
| 5,715,844 | A | | 2/1998 | Young | |
| 5,724,998 | A | | 3/1998 | Gellatly | |
| 5,765,570 | A | | 6/1998 | Litzinger | |
| 5,810,020 | A | | 9/1998 | Northway | |
| 5,873,372 | A | * | 2/1999 | Honeycutt | A24B 3/182 131/309 |
| 5,908,034 | A | | 6/1999 | Adedeji | |
| 6,216,706 | B1 | | 4/2001 | Kumar | |
| 6,679,270 | B2 | | 1/2004 | Baskevitch | |
| 2008/0178894 | A1 | * | 7/2008 | Zimmermann | A24B 15/24 131/298 |
| 2010/0206317 | A1 | * | 8/2010 | Albino | A24D 1/00 131/202 |
| 2012/0125354 | A1 | * | 5/2012 | Byrd | A24B 15/24 131/297 |

FOREIGN PATENT DOCUMENTS

| | | | | |
|---|---|---|---|---|
| EP | 2687110 | | 1/2014 | |
| JP | 2002-503965 | | 2/2002 | |
| JP | 2001-525190 | | 12/2011 | |
| WO | WO 98/58555 | | 12/1998 | |
| WO | WO-2008068153 A2 | * | 6/2008 | A24B 15/245 |
| WO | WO 2012/124059 | | 9/2012 | |
| WO | WO 2012160133 | | 11/2012 | |

OTHER PUBLICATIONS

PCT Search Report and Written Opinion for PCT/EP2014/055209 dated Jul. 23, 2014 (11 pages).

MacKown et al. (1988) J. Agric. Food Chem. 36, 1031-1035.

Haut, S. A., Lambert, E. A., 1988, The Determination of TSNA in Fillers from the Crossed Soluble/Baseweb Study. Legacy Tobacco Documents Library.

Keene, C.K., 1992, The Effect of Base Digestion on TSNA in Extractables-Depleted Fillers. Legacy Tobacco Documents.

Tobacco Encyclopedia, Voges (Ed.) p. 44-45 (1984).

Browne, The Design of Cigarettes, 3rd Ed., p. 43 (1990).

Tobacco Production, Chemistry and Technology, Davis et al. (Eds.) p. 346 (1999).

Office Action issued in Japan for Application No. 2015-562249 dated Aug. 29, 2018 (4 pages). English translation included.

PCT International Preliminary Report on Patentability for PCT/EP2014/055209 dated Sep. 11, 2015 (7 pages).

* cited by examiner

METHODS FOR REDUCING ONE OR MORE TOBACCO SPECIFIC NITROSAMINES IN TOBACCO MATERIAL

This application is a U.S. National Stage Application of International Application No. PCT/EP2014/055209, filed Mar. 14, 2014, which was published in English on Sep. 18, 2014 as International Patent Publication WO 2014/1403346. International Application No. PCT/EP2014/055209 claims priority to European Application No. 13159620.7 filed Mar. 15, 2013.

FIELD OF THE INVENTION

The present invention relates to methods for reducing the amount of one or more types of tobacco specific nitrosamines, including 4-(methylnitrosamino)-1-(3-pyridyl)-1-butanone (NNK), in tobacco material. Tobacco products comprising tobacco material obtained or obtainable by said methods are also described.

BACKGROUND OF THE INVENTION

During the manufacture and processing of tobacco products, by-products such as tobacco stems, leaf scraps, and tobacco dust produced during the manufacturing process (including stemming, aging, blending, cutting, drying, cooling, screening, shaping and packaging) are produced and can be recycled to reclaim their useful tobacco content. For example, tobacco stems and tobacco fines from manufacturing processes are unsuitable for use directly in the manufacturing of tobacco products. Since the stems and fines represent a substantial amount of raw material investment, processes have been developed to further convert these stems and fines into products such as reconstituted tobacco sheets which are then useable in relatively large amounts in a mixture with acceptable processed tobacco leaf. Reconstituted tobacco can be manufactured in a slurry or cast sheet process wherein pulp of mashed tobacco stems and other parts of the tobacco leaf are ground and mixed with a solution that might contain different additives. The resulting tobacco slurry is then sprayed to form a thin film, dried, rolled and diced into strips which are added to a filler.

Nitrosamines are organic compounds found in many consumer products, such as tobacco, food products and cosmetics. Nitrosamines have drawn intense scientific interest because some of the compounds in this class have been shown to be carcinogenic in laboratory animals. It has been reported that air-cured and flue-cured tobaccos contain tobacco specific nitrosamines which can be found in smokeless tobacco, mainstream smoke and side stream smoke of cigarettes. In tobacco, four species of nitrosamines are produced at appreciable quantity. These are 4-(methylnitrosamino)-1-(3-pyridyl)-1-butanone (NNK), N-nitrosonornicotine (NNN), N-nitrosoanatabine (NAT), and N-nitrosoanabasine (NAB). Tobacco specific nitrosamines are not considered to be present in significant quantities in growing tobacco plants or fresh cut tobacco (green tobacco), but can be formed during the curing process. In addition to the formation of tobacco specific nitrosamines during the curing process of green leaves, tobacco specific nitrosamines may also be formed during processes used to prepare aqueous tobacco slurries—such as processes used to prepare reconstituted tobacco.

In an attempt to reduce tobacco specific nitrosamines, various treatments of tobacco plants or harvested tobacco leaves have been suggested, including radiation treatments, chemical treatments and extractions. Other methods for reducing tobacco specific nitrosamines have been suggested by MacKown et al. (1988) *J. Agric. Food Chem.* 36, 1031-1035. These methods involve treatment using sterilization, microbial inhibitors, bases to increase pH, or ascorbic acid to decrease the accumulation of tobacco specific nitrosamines during the production of reconstituted tobacco sheets. WO2012160133 describes a process for decreasing the levels of tobacco specific nitrosamines in tobacco homogenates by increasing the pH thereof, especially when elevated levels of nitrosamines are created by elevated nitrite levels.

One problem with trying to reduce the levels of one or more tobacco specific nitrosamines in tobacco is that some of the nitrosamines in air-cured tobacco, including NNK, exist in a matrix-bound form. For example, the smoke of Burley baseweb (i.e. water-extracted Burley fibers) contains 70% of the NNK found in the smoke of the original tobacco, while NNN and NAT levels are reduced by more than 95% (Haut, S. A., Lambert, E. A., 1988, The Determination of TSNA in Fillers from the Crossed Soluble/Baseweb Study. Legacy Tobacco Documents Library). Matrix bound NNK can be extracted with 0.1N KOH solution from water-washed Burley filler. This alkaline treatment also decreases NNK levels in smoke (Keene, C. K., 1992, The Effect of Base Digestion on TSNA in Extractables-Depleted Fillers. Legacy Tobacco Documents). However, the treatment can introduce toxicologically relevant compounds into tobacco and significantly deteriorates the quality of the tobacco. The matrix bound form cannot be easily solubilised using pH neutral aqueous extraction methods.

A need remains for an effective and cost efficient method for reducing tobacco specific nitrosamines, particularly those tobacco specific nitrosamines, including NNK, that are formed during the processing of tobacco and are in the matrix-bound form.

SUMMARY OF THE INVENTION

The present invention is based, at least in part, on the surprising finding that tobacco specific nitrosamines, including matrix-bound tobacco specific nitrosamines, suitably, matrix-bound NNK, can be released by heating tobacco and tobacco-derived materials to temperatures above 100° C. Generally, the heating step is performed in the presence of liquid—such as water or steam. In certain embodiments, water, for example, heated water in the form of steam, is exclusively used. The matrix-bound tobacco specific nitrosamine(s), including matrix-bound NNK, that is released can be readily removed by washing which can result in a tobacco material with a lower tobacco specific nitrosamine(s) content, concentration or amount than the untreated starting material. It can also result in a tobacco material that produces lower tobacco specific nitrosamine concentrations in aerosol, including smoke, than the untreated starting material. Accordingly, the same matrix-bound NNK which is released upon heating is also transferred to the aerosol during smoking. Advantageously, this method can be applied to many types of different tobacco materials and especially tobacco materials with high-tobacco specific nitrosamine values. In particular, the method can be applied to high-tobacco specific nitrosamine, low-value material, including stems or fibers that are used in certain tobacco processes. In contrast to other methods utilizing water or organic solvents at temperatures below 100° C., the proposed process can remove tobacco specific nitrosamines that are bound to the insoluble polymeric matrix of tobacco. It is also advantageous that the method can be carried out in certain embodiments without the use of any additives and thereby does not introduce any additional toxicologically relevant compounds into the tobacco. One general object of this disclosure is to substantially eliminate, decrease or reduce the content of nitrosamine(s), including NNK, in tobacco intended for smoking or consumption by other means. Another general object is to reduce the carcinogenic potential of tobacco products, including cigarettes, cigars, chewing tobacco, snuff and tobacco-containing gum and lozenges. Still another general object is to substantially eliminate, decrease or reduce the amount of tobacco-specific nitrosamines, including NNK, in tobacco products. Another general object is to reduce the content of tobacco-specific nitrosamine(s) in fully cured tobacco. Another general object is to reduce the content of tobacco-specific nitrosamine(s) in aerosol, including smoke. Yet another object of this disclosure is to reduce the content of one or more tobacco specific nitrosamines, including NNK, and metabolites thereof in humans who smoke, consume or otherwise ingest tobacco in some form, by providing a tobacco product suitable for human consumption which contains a substantially reduced quantity of tobacco-specific nitrosamine(s), thereby lowering the carcinogenic potential of such product.

In a first aspect, there is provided a method of reducing the amount of at least matrix-bound NNK in tobacco material comprising the steps of: (a) providing tobacco material comprising at least matrix-bound NNK; (b) optionally measuring the level of at least matrix-bound NNK in the tobacco material; (c) heating the tobacco material for at least about 30 seconds to a temperature of greater than about 100 degrees Celsius or greater than about 110 degrees Celsius in the presence of a liquid or steam to release at least a portion of the matrix-bound NNK from the insoluble tobacco matrix of the tobacco material; (d) optionally measuring the level of at least matrix-bound NNK in the tobacco material following step (c); (e) optionally comparing the levels of matrix-bound NNK obtained in steps (b) and (d); and (f) identifying tobacco material in which at least matrix-bound NNK has been released or removed from the tobacco material.

In one embodiment, the method comprises the further steps of washing the tobacco material with a first aqueous solution or solvent before step (c) and washing the tobacco material with a second aqueous solution or solvent after step (c).

In one embodiment, the tobacco material provided in step (a) is contacted with a first aqueous solution or solvent prior to step (c).

In one embodiment, the matrix-bound NNK is removed from the sample by one or more washes with a second aqueous solution or solvent.

In one embodiment, the first and/or second aqueous solution or solvent is the same of different.

In one embodiment, the method may comprise the further step between steps (a) and (b) of combining the tobacco material with a first aqueous solution or solvent. This can form a mixture.

In one embodiment, the tobacco material that is heated in step (a) is contacted with an aqueous solution or solvent. For example, the tobacco material can be wetted or wet. For example, the tobacco material can be in the form of an at least 5% (w/v) aqueous mixture, such as a solution or a suspension.

In one embodiment, step (b) comprises heating the aqueous mixture containing the tobacco material. In one embodiment, at least a portion of the NNK is initially bound to an insoluble tobacco matrix in the tobacco material and the heating step (b) releases at least a portion of the NNK from the insoluble tobacco matrix.

In one embodiment, the method comprises the further step of: (c) removing at least a portion of the released NNK from the tobacco material. In one embodiment, the NNK is released from the sample by one or more washes with a second aqueous solution or solvent.

In one embodiment, the tobacco material provided in step (a) is contacted with a first aqueous solution or solvent prior to use.

In one embodiment, the aqueous solution is a solvent.

In one embodiment, the tobacco material is selected from the group consisting of: tobacco leaf and/or tobacco stems and/or tobacco dust and/or tobacco leaf prime lamina strip or a combination of two or more thereof.

In one embodiment, the tobacco material is heated in the presence of water or steam produced from water.

In another embodiment, the tobacco material is heated in the presence of water, steam or both water and steam.

In another embodiment, the tobacco material is heated in the presence of water and/or steam under pressure. Exemplary pressure levels are between about 1 and at least about 40 psi, between about 5 and at least about 40 psi and between 10 and at least about 40 psi.

In another embodiment, the tobacco material is heated using pressurised saturated steam.

In another embodiment, the tobacco material is heated using superheated steam.

In a further aspect there is provided a tobacco material obtained or obtainable by the method described herein.

In a further aspect there is provided (treated or processed) tobacco material comprising less than about 2400 ng/g NNK in the insoluble tobacco matrix and at least about 1000 ng/g free NNK.

In a further aspect there is provided (treated or processed) tobacco material in which the amount or concentration of matrix-bound NNK is at least 10%, 20%, 30%, 40%, 50%, 60%, 70%, 80%, 90% or 100% lower as compared to untreated or unprocessed tobacco material.

In a further aspect there is provided a method for reducing the amount or concentration of one or more tobacco specific nitrosamines in an aerosol comprising the steps of: (a) providing tobacco material comprising one or more tobacco specific nitrosamines; (b) heating the tobacco material for at least about 30 seconds to a temperature of greater than about 100 degrees Celsius in the presence of a liquid or steam to release at least a portion of the one or more tobacco specific nitrosamines from the insoluble tobacco matrix of the tobacco material; (c) removing at least a portion of the released tobacco specific nitrosamine(s) from the tobacco material; and (d) heating the tobacco material from step (b) to produce an aerosol. Suitably, the aerosol that is obtained has a lower level of NNK as compared to an aerosol from a control tobacco material that has not been subjected to at least step (b).

In a further aspect there is provided a method for reducing the amount or concentration of one or more tobacco specific nitrosamines in an aerosol comprising the steps of: (a) providing tobacco material comprising one or more tobacco specific nitrosamines; (b) heating the tobacco material for at least about 30 seconds to a temperature of greater than about 100 degrees Celsius in the presence of a liquid or steam to release at least a portion of the tobacco specific nitrosamine(s) from the insoluble tobacco matrix of the tobacco material; (c) removing at least a portion of the released tobacco specific nitrosamine(s) from the tobacco material; and (d) heating the tobacco material from step (b) to produce an aerosol. Suitably, the aerosol that is obtained has a lower level of NNK as compared to an aerosol from a control tobacco material that has not been subjected to at least step (b).

In a further aspect there is provided an aerosol obtained or obtainable by the method described herein.

In a further aspect, there is provided a method for producing reconstituted tobacco comprising the steps of: (a) providing tobacco material comprising one or more tobacco specific nitrosamines; (b) heating the tobacco material for at least about 30 seconds to a temperature of greater than about 100 degrees Celsius in the presence of a liquid or steam to release at least a portion of the tobacco specific nitrosamine(s) from the insoluble tobacco matrix of the tobacco material; (c) washing the tobacco material from step (b) with an aqueous solution or solvent to release the tobacco specific nitrosamine(s) from the tobacco material; (d) manufacturing the tobacco material obtained from step (c) into reconstituted tobacco; and (d) optionally incorporating the reconstituted tobacco into a tobacco product.

In a further aspect, there is provided a method for producing reconstituted tobacco comprising the steps of: (a) providing tobacco material comprising one or more tobacco specific nitrosamines; (b) manufacturing said tobacco material into reconstituted tobacco by separating tobacco fibres from soluble material; (c) heating the separated fibres for at least about 30 seconds to a temperature of at least 100 degrees Celsius in the presence of a liquid or steam to release at least a portion of the tobacco specific nitrosamine(s) from the insoluble tobacco matrix of the separated fibres; (d) washing the fibres with an aqueous solution or solvent; (e) recombining the fibres and soluble material to form a reconstituted tobacco sheet; and (f) optionally incorporating the reconstituted tobacco into a tobacco product.

In a further aspect there is provided a method for producing reconstituted tobacco comprising the steps of: (a) providing tobacco material comprising one or more tobacco specific nitrosamines; and (b) heating the tobacco material for at least about 30 seconds to a temperature of greater than about 100 degrees Celsius in the presence of a liquid or steam to release at least a portion of the tobacco specific nitrosamine(s) from the insoluble tobacco matrix of the tobacco material; (c) removing at least a portion of the released tobacco specific nitrosamine(s) from the tobacco material; (d) casting the tobacco material into one or more sheets; (e) drying the cast sheet(s); and (f) optionally incorporating the sheet(s) into a tobacco product.

In a further aspect there is provided reconstituted tobacco obtained or obtainable by the method described herein.

In a further aspect there is provided a method for preparing tobacco for use as a tobacco cut filler comprising the steps of: (a) providing tobacco material—such as tobacco stems—comprising one or more tobacco specific nitrosamines; (b) heating the tobacco material for at least about 30 seconds to a temperature of greater than about 100 degrees Celsius in the presence of a liquid or steam to release at least a portion of the tobacco specific nitrosamine(s) from the insoluble tobacco matrix of the tobacco material; (c) removing at least a portion of the released tobacco specific nitrosamine(s) from the tobacco material; and (d) rolling and cutting the tobacco material.

In a further aspect there is provided a method of producing cut filler comprising rolled tobacco stems comprising the steps of: (a) providing tobacco stems comprising one or more tobacco specific nitrosamines; (b) heating the tobacco stems for at least about 30 seconds to a temperature of greater than about 100 degrees Celsius in the presence of a liquid or steam to release at least a portion of the tobacco specific nitrosamine(s) from the insoluble tobacco matrix of the tobacco stems; (c) removing at least a portion of the released tobacco specific nitrosamine(s) from the tobacco stems; (d) blending the treated stems with at least one type of tobacco lamina, expanded tobacco or reconstituted tobacco; and (e) producing cut filler.

In a further aspect there is provided a tobacco cut filler obtained or obtainable by the method described herein.

In a further aspect, there is provided a method of reducing the amount of at least matrix-bound NNK in tobacco material comprising the steps of: (a) providing tobacco material comprising at least matrix-bound NNK; (b) washing the tobacco material with a first aqueous solution or solvent; (c) heating the tobacco material for at least about 30 seconds to a temperature of greater than about 100 degrees Celsius or 110 degrees Celsius in the presence of a liquid or steam to release at least a portion of the matrix-bound NNK from the insoluble tobacco matrix of the tobacco material; (d) washing the tobacco material from step (c) with a second aqueous solution; and (e) removing or releasing at least matrix-bound NNK from the tobacco material. Each of the embodiments discussed above are disclosed as embodiments of each of the aspects of the invention. Combinations of one or of the embodiments are contemplated.

DEFINITIONS

Figure 1:
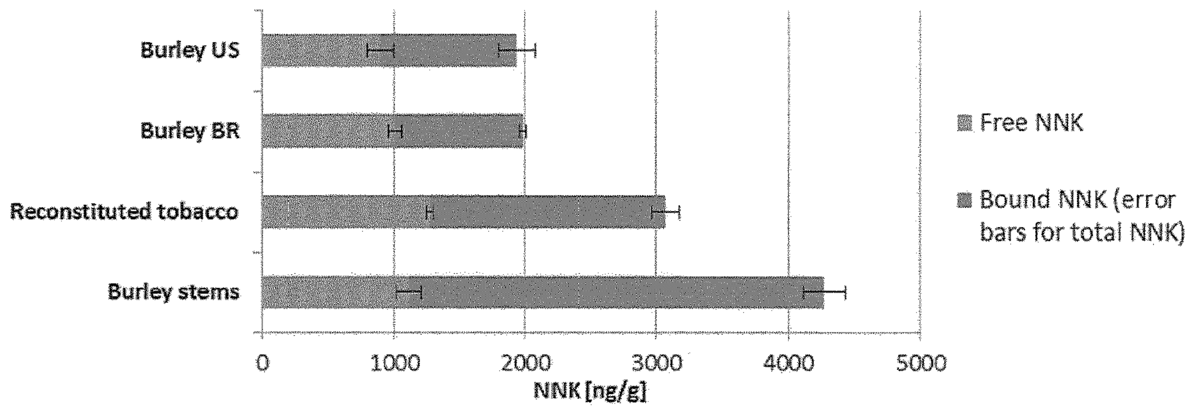
FIG. 1 shows the free and matrix-bound NNK concentrations in selected tobacco samples.

The technical terms and expressions used within the scope of this application are generally to be given the meaning commonly applied to them in the pertinent art of plant and molecular biology. All of the following term definitions apply to the complete content of this application. The word "comprising" does not exclude other elements or steps, and the indefinite article "a" or "an" does not exclude a plurality. A single step may fulfil the functions of several features recited in the claims. The terms "essentially", "about", "approximately" and the like in connection with an attribute or a value particularly also define exactly the attribute or exactly the value, respectively. The term "about" in the context of a given numerate value or range refers to a value or range that is within 20%, within 10%, or within 5% of the given value or range.

The terms "reduce", "reduced" "inhibit" or "inhibited" as used herein, includes a reduction of at least about 5%, at least about 10%, at least about 20%, at least about 30%, at least about 40%, at least about 50%, at least about 60%, at least about 70%, at least about 75%, at least about 80%, at least about 90%, at least about 95%, at least about 98%, at least about 99% or up to 100% of a quantity.

The term "at least a portion" as used herein, includes at least about 5%, at least about 10%, at least about 20%, at least about 30%, at least about 40%, at least about 50%, at least about 60%, at least about 70%, at least about 75%, at least about 80%, at least about 90%, at least about 95%, at least about 98%, or at least about 99% of a quantity.

The term "tobacco material" refers to any part of a tobacco plant or a mixture of different tobacco plants and includes without limitation tobacco leaf scraps, tobacco green leaf scraps, tobacco stems, tobacco dust created during tobacco processing, and tobacco leaf prime lamina strip and a combination thereof. The tobacco material can have the form of processed tobacco parts or pieces, cured and aged tobacco in essentially natural lamina or stem form, a tobacco extract or a mixture of the foregoing, for example, a mixture that combines extracted tobacco pulp with granulated cured and aged natural tobacco lamina. The tobacco material can be in solid form, in liquid form, in semi-solid form, or the like. The tobacco material can be in the form of a tobacco homogenate that has been subjected to homogenization, including, but not limited to cutting and grinding. The tobacco homogenate may be prepared from whole tobacco plants or from mixtures of plant components—such as a mixture of stems and leaves—that have been subjected to homogenisation. The tobacco material can be in the form of a tobacco slurry, including a suspension of tobacco material or a tobacco homogenate in an aqueous solution or solvent. The slurry can be a 5% (w/v), 10% (w/v), 15% (w/v), 20% (w/v) or 25% (w/v) or more mixture of tobacco in an aqueous solution or solvent.

The term "tobacco product" includes smoking or smokable articles, and smokeless tobacco products.

The term "free nitrosamine" or grammatical variations thereof as used herein refers to the nitrosamine concentration calculated in extracts of tobacco.

The term "total nitrosamine" or grammatical variations thereof as used herein refers to the nitrosamine concentration calculated after subjecting the extraction mixtures to the methods described herein (for example, by heating to about 130° C. for about 4 hours).

The term "bound nitrosamine" or "matrix-bound nitrosamine" or grammatical variations thereof as used herein represents the difference between the "total nitrosamine" and the "free nitrosamine" concentrations.

DETAILED DESCRIPTION

The present invention is applicable to the treatment of harvested tobacco that is intended for human consumption. Generally speaking, the methods can be applied to any form of tobacco material comprising tobacco specific nitrosamine(s), including NNK. Suitably, at least a portion of the tobacco specific nitrosamine(s) are bound to the insoluble tobacco matrix. Suitably, at least a portion of NNK is bound to the insoluble tobacco matrix. Methods for measuring free nitrosamine(s) and nitrosamine(s) bound to the insoluble tobacco matrix are well known in the art and described herein. Briefly, aliquots of tobacco samples are extracted and the nitrosamine content therein is analysed using ultra performance liquid chromatography-tandem mass (UPLC-MS/MS). Typically, one or more standards corresponding to the nitrosamines that are being quantified will be incorporated into the aliquots of the tobacco samples. The sample concentrations calculated from the extracts corresponds to the "free NNK" concentrations in the sample. After treating the extraction mixtures to the methods described herein (for example, by heating to about 130° C. for about 4 hours) nitrosamine concentrations are again measured by UPLC-MS/MS. From these values, the "total NNK" concentration in the samples can be calculated. The "bound NNK" concentration is the difference between the "total NNK" and the "free NNK" concentrations. Much research has been performed on tobacco, especially in relation to tobacco-specific nitrosamines. Freshly harvested tobacco leaves are referred to as "green tobacco" and are believed to contain no known carcinogens, but green tobacco is not suitable for human consumption. The process of curing green tobacco depends on the type of tobacco harvested. For example, Virginia flue (bright) tobacco is typically flue-cured, whereas Burley and certain dark strains are usually air-cured. The flue-curing of tobacco typically takes place over a period of five to seven days compared to one to two months for air-curing. Many major chemical and biochemical changes begin during the curing process and continue through the early phases of leaf drying. The conversion of the tobacco from its yellow to brown colour generally results in formation and substantial accumulation of nitrosamines, and an increased microbial content. The exact mechanism by which tobacco-specific nitrosamines are formed is not clear, but is believed to be enhanced by microbial activity, involving microbial nitrate reductases in the generation of nitrite during the curing process.

According to one embodiment, the present invention provides methods for reducing the level, amount or concentration of one or more tobacco specific nitrosamines in tobacco material. According to another embodiment, the present invention provides methods for reducing the level, amount or concentration of at least NNK in tobacco material. According to one embodiment, the present invention provides methods for reducing the level, amount or concentration of one or more tobacco specific nitrosamines in tobacco material—such as NNK—that are bound to the insoluble matrix.

In one aspect, there is provided a method of reducing the amount of one or more tobacco specific nitrosamines in tobacco material comprising the steps of: (a) providing tobacco material comprising one or more tobacco specific nitrosamines; (b) optionally combining (for example, mixing) the tobacco material with a first aqueous solution or solvent; and (c) heating the tobacco material for at least about 30 seconds to a temperature of greater than about 100 degrees Celsius or 101 degrees Celsius in the presence of a liquid or steam to release at least a portion of the tobacco specific nitrosamine(s) from the insoluble tobacco matrix of the tobacco material. In one embodiment, the tobacco material that is heated in step (c) is wetted or wet. For example, the tobacco material can be in the form of an at least 5% (w/v) mixture. In one embodiment, step (c) comprises heating the mixture containing the tobacco material from step (b). At least a portion of the released tobacco specific nitrosamine(s) is released from the tobacco material by one or more washings steps. The method can reduce the total amount of one or more tobacco specific nitrosamines in tobacco material. As discussed above, tobacco specific nitrosamines include 4-(methylnitrosamino)-1-(3-pyridyl)-1-butanone (NNK), N-nitrosonomicotine (NNN), N-nitrosoanatabine (NAT), and N-nitrosoanabasine (NAB). The method can reduce the total amount of at least NNK in tobacco material. The method can reduce the total amount of one or more tobacco specific nitrosamines that are bound to the insoluble matrix in tobacco material. The method can reduce the total amount of at least NNK that is bound to the insoluble matrix in tobacco material.

In one embodiment, the tobacco material can be used in the preparation of reconstituted tobacco, such as reconstituted tobacco (leaf) sheets. These sheets are paper-like material that can be made from recycled tobacco fines, tobacco stems and "class tobacco", which consists of tobacco particles generally less than 30 mesh in size that are collected at any stage of tobacco processing. The reconstituted tobacco can be made by extracting the soluble chemicals in the tobacco by-products, processing the leftover tobacco fibers from the extraction into a paper, and then reapplying the extracted materials in concentrated form onto the paper.

Thus, in one aspect, there is provided a method for producing reconstituted tobacco comprising the steps of: (a) providing tobacco material comprising one or more tobacco specific nitrosamines; (b) heating the tobacco material for at least about 30 seconds to a temperature of greater than about 100 degrees Celsius in the presence of a liquid or steam to release at least a portion of the tobacco specific nitrosamine(s) from the insoluble tobacco matrix of the tobacco material; (c) removing at least a portion of the released tobacco specific nitrosamine(s) from the tobacco material; (d) manufacturing the tobacco material obtained from step (c) into reconstituted tobacco; and (e) optionally incorporating the reconstituted tobacco into a tobacco product.

In a further aspect, there is provided a method for producing reconstituted tobacco comprising the steps of: (a) providing tobacco material comprising one or more tobacco specific nitrosamines; (b) optionally combining the tobacco material with a first aqueous solution or solvent; (c) heating the tobacco material for at least about 30 seconds to a temperature of greater than about 100 degrees Celsius in the presence of a liquid or steam to release at least a portion of the tobacco specific nitrosamine(s) from the insoluble tobacco matrix of the tobacco material; (d) removing at least a portion of the released tobacco specific nitrosamine(s) from the tobacco material; (e) removing at least a portion of the released tobacco specific nitrosamine(s) from the tobacco material; (f) casting the tobacco material into one or more sheets; (g) drying the cast sheet(s); and (h) optionally incorporating the sheet(s) into a tobacco product.

In one embodiment, the tobacco material comprises or consists or consists essentially of cured tobacco material. Processes of curing tobacco leaves, especially, green tobacco leaves are well known to those skilled in the art and include without limitation air-curing, fire-curing, flue-curing and sun-curing. The process of curing tobacco material depends on the type of tobacco harvested. For example, Virginia flue (bright) tobacco is typically flue-cured, Burley and certain dark strains are usually air-cured, and pipe tobacco, chewing tobacco, and snuff are usually fire-cured. Although tobacco material from any type of tobacco may be used, certain types of tobacco are preferred. Particularly preferred tobacco materials are selected from the group consisting of: flue-Cured, Turkish, Burley, Virginia, Maryland, Oriental, or any combination of two or more thereof. The shape of the tobacco material is not limited. It can be in the form of homogenised tobacco material. It can be in the form of a ground tobacco material. It can even be in the form of a finely ground tobacco material. Finely ground tobacco material typically has a particle size of from about 30 to 600 microns. Finely ground tobacco material may be obtained from any of the processes known for manufacturing tobacco products as an incidental by-product of these processes or may be obtained by a further size reduction process such as a grinding technique including impact grinding and roller grinding. Tobacco homogenates—such as but not limited to cured tobacco homogenates—may be prepared from tobacco material using various methods known in the art, for example, the tobacco may be in a shredded, ground, granulated, fine particulate, or powder form. The tobacco may be employed in the form of parts or pieces that have an average particle size less than that of the parts or pieces of shredded tobacco used in so-called "fine cut" tobacco products. If the tobacco is formed into very finely divided tobacco particle or piece then they may be sized to pass through a screen of about 18 Tyler mesh, about 20 Tyler mesh, about 50 Tyler mesh, about 60 Tyler mesh, about 100 Tyler mesh, or about 200 Tyler mesh or more. If desired, differently sized tobacco homogenates may be mixed together. Suitably, tobacco homogenates are ground or pulverized into a powder type of form using equipment and techniques for grinding, milling, or the like. Suitably, the tobacco is relatively dry in form during grinding or milling, using equipment such as hammer mills, cutter heads, air control mills, or the like. For example, tobacco parts or pieces may be ground or milled when the moisture content thereof is less than about 15 weight percent to less than about 5 weight percent. The tobacco material may be formed with parts of the tobacco leaves—such as the lamina and stems or with tobacco stems, tobacco leaves and tobacco dust.

Prior to use, the tobacco material can optionally be pre-washed or contacted with a first aqueous solution or solvent. In certain embodiments, the first aqueous solution is a non-toxic aqueous solution comprising water. In certain embodiments, the first aqueous solution is exclusively water. In certain embodiments, the first aqueous solution is a buffer or a non-toxic aqueous solution containing the buffer. If a buffer is used then it will generally be at a desirable pH—such as at least about pH 5.0, pH 6.0 or pH 7.0 or more. The first aqueous solution or solvent when combined or mixed with the tobacco material can be, for example, a 5% (w/v), 10% (w/v), 15% (w/v), 20% (w/v), 25% (w/v), 30% (w/v), 35% (w/v), 40% (w/v) or 45% (w/v) or more mixture. In certain embodiments a mixture of ratio 1:5 or 1:10 tobacco material: aqueous solution or solvent is used. In certain embodiments, the pre-washing step is carried out for at least about 5, 10, 15, 20, 25, 30, 35, 40, 45, 50, 55, 60, 90, 120, 150 or 180 minutes or more at about room temperature. In certain embodiments, the pre-washing step is carried out at about room temperature or temperatures that are higher or lower than room temperature—such as about 20 degrees Celsius, about 30 degrees Celsius, about 40 degrees Celsius, about 50 degrees Celsius, about 60 degrees Celsius, about 80 degrees Celsius, or about 90 degrees Celsius or higher. In certain embodiments, the pre-washing step can be carried out in the presence of physical agitation and/or more stringent washing conditions—such as higher temperature and/or rigorous physical agitation. It is considered that more stringent washing conditions could further reduce the total tobacco specific nitrosamine content.

The tobacco material can be combined with an aqueous solution or solvent to form a mixture. The aqueous solution or solvent can be the same or different to the first aqueous solution or solvent used in the pre-washing or contacting step. The tobacco material can be used to form a tobacco slurry or a cured tobacco slurry. A tobacco slurry can be prepared by mixing the tobacco material, including homogenised or grounded tobacco material, with an aqueous solution or solvent. The exact type or nature of the aqueous solution or solvent is not limiting although it is an advantage of the present invention that the aqueous solution or solvent does not introduce any additional toxicologically relevant compounds into the tobacco. Thus, the aqueous solution or solvent will generally not be toxic to human health at the concentrations used in the treatment process. In certain embodiments, the aqueous solution is a non-toxic aqueous solution containing water. In certain embodiments, the aqueous solution is a buffer or a non-toxic aqueous solution containing the buffer. If a buffer is used then it will be at a desirable pH—such as at least about pH 6.0 or pH 7.0 or more. The aqueous solution or solvent when combined with the tobacco material can be, for example, a 5% (w/v), 10% (w/v), 15% (w/v), 20% (w/v), 25% (w/v), 30% (w/v), 35% (w/v), 40% (w/v) or 45% (w/v) or more mixture.

In a further step of the method, the tobacco material can be heated for at least about 10 seconds, 20 seconds, 30 seconds, 40 seconds, 50 seconds or 1, 2, 3, 4, 5, 6, 7, 8, 9, 10, 11, 12, 13, 14, 15, 16, 17, 18, 19, 20, 25, 30, 40, 45, 50, 60 minutes or 2, 3, 4, 5, 6, 7, or 8 or more hours to a temperature of greater than about 100 degrees Celsius to release at least a portion of NNK from the insoluble tobacco matrix into the tobacco material. Generally the heating step is carried out in the presence of a liquid which can become steam at a temperature of greater than about 100 degrees Celsius to release at least a portion of the tobacco specific nitrosamine(s) from the insoluble tobacco matrix of the tobacco material. Suitably, the tobacco material that is heated is wetted or wet before heating. For example, the tobacco material can be in the form of an at least 5% (w/v) mixture. Suitably, the tobacco material is in the form of the mixture described herein and this mixture is heated for at least about 10 seconds, 20 seconds, 30 seconds, 40 seconds, 50 seconds or 1, 2, 3, 4, 5, 6, 7, 8, 9, 10, 11, 12, 13, 14, 15, 16, 17, 18, 19, 20, 25, 30, 40, 45, 50, 60 minutes or 2, 3, 4, 5, 6, 7, or 8 or more hours or more to a temperature of greater than about 100 degrees Celsius as described herein or to a temperature greater than about 200 degrees Celsius as described herein to release at least a portion of NNK from the insoluble tobacco matrix into the tobacco material. The tobacco material, the wetted or wet tobacco material or the mixture comprising the tobacco material can be heated for at least about 10 seconds, 20 seconds, 30 seconds, 40 seconds, 50 seconds or 1, 2, 3, 4, 5, 6, 7, 8, 9, 10, 11, 12, 13, 14, 15, 16, 17, 18, 19, 20, 25, 30, 40, 45, 50, 60 minutes or 2, 3, 4, 5, 6, 7, or 8 or more hours to a temperature of greater than about 100 degrees Celsius to release at least a portion of one or more tobacco specific nitrosamines—such as NNK—from the insoluble tobacco matrix into the tobacco material. In certain embodiments, the tobacco material, the wetted or wet tobacco material or the mixture comprising the tobacco material is heated for at least about 30 seconds to a temperature of greater than about 100 degrees Celsius. In certain embodiments, the tobacco material, the wetted or wet tobacco material or the mixture comprising the tobacco material is heated for at least about 1 minute to a temperature of greater than about 100 degrees Celsius. In certain embodiments, the tobacco material, the wetted or wet tobacco material or the mixture comprising the tobacco material is heated for at least about 5 minutes to a temperature of greater than about 100 degrees Celsius. In certain embodiments, the tobacco material, the wetted or wet tobacco material or the mixture comprising the tobacco material is heated for at least about 10 minutes to a temperature of greater than about 100 degrees Celsius. In certain embodiments, the tobacco material, the wetted or wet tobacco material or the mixture comprising the tobacco material is heated for at least about 20 minutes to a temperature of greater than about 100 degrees Celsius. In certain embodiments, the tobacco material, the wetted or wet tobacco material or the mixture comprising the tobacco material is heated for at least about 30 minutes to a temperature of greater than about 100 degrees Celsius. In certain embodiments, the tobacco material, the wetted or wet tobacco material or the mixture comprising the tobacco material is heated for at least about 45 minutes to a temperature of greater than about 100 degrees Celsius. In certain embodiments, the tobacco material, the wetted or wet tobacco material or the mixture comprising the tobacco material is heated for at least about 60 minutes to a temperature of greater than about 100 degrees Celsius. In certain embodiments, the tobacco material, the wetted or wet tobacco material or the mixture comprising the tobacco material is heated for at least about 90 minutes to a temperature of greater than about 100 degrees Celsius. In certain embodiments, the tobacco material, the wetted or wet tobacco material or the mixture comprising the tobacco material is heated for at least about 120 minutes to a temperature of greater than about 100 degrees Celsius.

The temperature to which the tobacco material, the wetted or wet tobacco material or the mixture comprising the tobacco material is heated to can be greater than or equal to about 101, 102, 103, 104, 105, 106, 107, 108, 109 or 110 degrees Celsius. The temperature to which the tobacco material, the wetted or wet tobacco material or the mixture comprising the tobacco material is heated to can be greater than or equal to about 115, 120, 125, 130, 135, 140, 145, 150, 155, 160, 165, 170, 175, 180, 185, 190, 195 or 200 degrees Celsius. The temperature to which the tobacco material, the wetted or wet tobacco material or the mixture comprising the tobacco material is heated to can be within a range of temperatures. By way of example, the temperature to which the tobacco material, the wetted or wet tobacco material or the mixture comprising the tobacco material is heated to can be within a range of from about 101 to 200 degrees Celsius, about 101 to 190 degrees Celsius, about 101 to 180 degrees Celsius, about 101 to 170 degrees Celsius, about 101 to 160 degrees Celsius, about 101 to 150 degrees Celsius, about 101 to 140 degrees Celsius, about 101 to 130 degrees Celsius, about 101 to 120 degrees Celsius, or about 101 to 110 degrees Celsius, about 101 to 120 degrees Celsius. By way of further example, the temperature to which the tobacco material, the wetted or wet tobacco material or the mixture comprising the tobacco material is heated to can be within a range of from about 110 to 200 degrees Celsius, about 120 to 200 degrees Celsius, about 130 to 200 degrees Celsius, about 140 to 200 degrees Celsius, about 150 to 200 degrees Celsius, about 160 to 200 degrees Celsius, about 170 to 200 degrees Celsius, about 180 to 200 degrees Celsius or about 190 to 200 degrees Celsius. By way of further example, the temperature to which the tobacco material, the wetted or wet tobacco material or the mixture comprising the tobacco material is heated to can be within a range of from about 110 to 190 degrees Celsius, about 120 to 190 degrees Celsius, about 130 to 190 degrees Celsius, about 140 to 190 degrees Celsius, about 150 to 190 degrees Celsius, about 160 to 190 degrees Celsius, about 170 to 190 degrees Celsius, or about 180 to 190 degrees Celsius or about 190 to 200 degrees Celsius. By way of further example, the temperature to which the tobacco material, the wetted or wet tobacco material or the mixture comprising the tobacco material is heated to can be within a range of from about 110 to 180 degrees Celsius, about 120 to 180 degrees Celsius, about 130 to 180 degrees Celsius, about 140 to 180 degrees Celsius, about 150 to 180 degrees Celsius, about 160 to 180 degrees Celsius, or about 170 to 180 degrees Celsius. By way of further example, the temperature to which the tobacco material, the wetted or wet tobacco material or the mixture comprising the tobacco material is heated to can be within a range of from about 110 to 170 degrees Celsius, about 120 to 170 degrees Celsius, about 130 to 170 degrees Celsius, about 140 to 170 degrees Celsius, about 150 to 170 degrees Celsius, or about 160 to 170 degrees Celsius. By way of further example, the temperature to which the tobacco material, the wetted or wet tobacco material or the mixture comprising the tobacco material is heated to can be within a range of from about 110 to 160 degrees Celsius, about 120 to 160 degrees Celsius, about 130 to 160 degrees Celsius, about 140 to 160 degrees Celsius, or about 150 to 160 degrees Celsius. By way of further example, the temperature to which the tobacco material, the wetted or wet tobacco material or the mixture comprising the tobacco material is heated to can be within a range of from about 110 to 150 degrees Celsius, about 120 to 150 degrees Celsius, about 130 to 150 degrees Celsius, or about 140 to 150 degrees Celsius. By way of further example, the temperature to which the tobacco material, the wetted or wet tobacco material or the mixture comprising the tobacco material is heated to can be within a range of from about 110 to 140 degrees Celsius, about 120 to 140 degrees Celsius, or about 130 to 140 degrees Celsius. By way of further example, the temperature to which the tobacco material, the wetted or wet tobacco material or the mixture comprising the tobacco material is heated to can be within a range of from about 110 to 130 degrees Celsius, about 110 to 120 degrees Celsius. By way of further example, the temperature to which the tobacco material, the wetted or wet tobacco material or the mixture comprising the tobacco material is heated to can be within a range of from about 101 to 140 degrees Celsius, about 105 to 140 degrees Celsius, about 110 to 140 degrees Celsius, about 115 to 140 degrees Celsius, about 120 to 140 degrees Celsius, about 125 to 140 degrees Celsius, about 130 to 140 degrees Celsius or about 135 to 140 degrees Celsius. By way of further example, the temperature to which the tobacco material, the wetted or wet tobacco material or the mixture comprising the tobacco material is heated to can be within a range of from about 101 to 130 degrees Celsius, about 105 to 130 degrees Celsius, about 110 to 130 degrees Celsius, about 115 to 130 degrees Celsius, about 120 to 130 degrees Celsius, or about 125 to 130 degrees Celsius.

In certain embodiments, the tobacco material, the wetted or wet tobacco material or the mixture comprising the tobacco material is heated for at least about 30 seconds to a temperature of at least about 110 degrees Celsius. In certain embodiments, the tobacco material, the wetted or wet tobacco material or the mixture comprising the tobacco material is heated for at least about 1 minute to a temperature of at least about 110 degrees Celsius. In certain embodiments, the tobacco material, the wetted or wet tobacco material or the mixture comprising the tobacco material is heated for at least about 5 minutes to a temperature of at least about 110 degrees Celsius. In certain embodiments, the tobacco material, the wetted or wet tobacco material or the mixture comprising the tobacco material is heated for at least about 10 minutes to a temperature of at least about 110 degrees Celsius. In certain embodiments, the tobacco material, the wetted or wet tobacco material or the mixture comprising the tobacco material is heated for at least about 15 minutes to a temperature of at least about 110 degrees Celsius. In certain embodiments, the tobacco material, the wetted or wet tobacco material or the mixture comprising the tobacco material is heated for at least about 20 minutes to a temperature of at least about 110 degrees Celsius. In certain embodiments, the tobacco material, the wetted or wet tobacco material or the mixture comprising the tobacco material is heated for at least about 30 minutes to a temperature of at least about 110 degrees Celsius. In certain embodiments, the tobacco material, the wetted or wet tobacco material or the mixture comprising the tobacco material is heated for at least about 60 minutes to a temperature of at least about 110 degrees Celsius. In certain embodiments, the tobacco material, the wetted or wet tobacco material or the mixture comprising the tobacco material is heated for at least about 30 seconds to a temperature of at least about 120 degrees Celsius. In certain embodiments, the tobacco material, the wetted or wet tobacco material or the mixture comprising the tobacco material is heated for at least about 20 minutes to a temperature of at least about 120 degrees Celsius. In certain embodiments, the tobacco material, the wetted or wet tobacco material or the mixture comprising the tobacco material is heated for at least about 30 minutes to a temperature of at least about 120 degrees Celsius. In certain embodiments, the tobacco material, the wetted or wet tobacco material or the mixture comprising the tobacco material is heated for at least about 60 minutes to a temperature of at least about 120 degrees Celsius. In certain embodiments, the tobacco material, the wetted or wet tobacco material or the mixture comprising the tobacco material is heated for at least about 30 seconds to a temperature of at least about 130 degrees Celsius. In certain embodiments, the tobacco material, the wetted or wet tobacco material or the mixture comprising the tobacco material is heated for at least about 20 minutes to a temperature of at least about 130 degrees Celsius. In certain embodiments, the tobacco material, the wetted or wet tobacco material or the mixture comprising the tobacco material is heated for at least about 30 minutes to a temperature of at least about 130 degrees Celsius. In certain embodiments, the tobacco material, the wetted or wet tobacco material or the mixture comprising the tobacco material is heated for at least about 60 minutes to a temperature of at least about 130 degrees Celsius.

In certain embodiments, the temperature to which the tobacco material, the wetted or wet tobacco material or the mixture comprising the tobacco material is heated to can be greater than or equal to about 200, 210, 220, 230, 240, 250, 260, 270, 280, 290 or 300 degrees Celsius. The temperature to which the tobacco material, the wetted or wet tobacco material or the mixture comprising the tobacco material is heated to can be within a range of temperatures. By way of example, the temperature to which the tobacco material, the wetted or wet tobacco material or the mixture comprising the tobacco material is heated to can be within a range of from about 200 to 300 degrees Celsius, from about 200 to 290 degrees Celsius, from about 200 to 280 degrees Celsius, from about 200 to 270 degrees Celsius, from about 200 to 260 degrees Celsius from about 200 to 250 degrees Celsius.

In certain embodiments, the tobacco material, the wetted or wet tobacco material or the mixture comprising the tobacco material is heated for at least about 20 seconds to a temperature of at least about 200, 210, 220, 230, 240, 250, 260, 270, 280, 290 or 300 degrees Celsius. In certain embodiments, the tobacco material, the wetted or wet tobacco material or the mixture comprising the tobacco material is heated for at least about 30 seconds to a temperature of at least about 200, 210, 220, 230, 240, 250, 260, 270, 280, 290 or 300 degrees Celsius. In certain embodiments, the tobacco material, the wetted or wet tobacco material or the mixture comprising the tobacco material is heated for at least about 40 seconds to a temperature of at least about 200, 210, 220, 230, 240, 250, 260, 270, 280, 290 or 300 degrees Celsius. In certain embodiments, the tobacco material, the wetted or wet tobacco material or the mixture comprising the tobacco material is heated for at least about 1 minute to a temperature of at least about 200, 210, 220, 230, 240, 250, 260, 270, 280, 290 or 300 degrees Celsius. In certain embodiments, the tobacco material, the wetted or wet tobacco material or the mixture comprising the tobacco material is heated for at least about 5 minutes to a temperature of at least about 200, 210, 220, 230, 240, 250, 260, 270, 280, 290 or 300 degrees Celsius. In certain embodiments, the tobacco material, the wetted or wet tobacco material or the mixture comprising the tobacco material is heated for at least about 10 minutes to a temperature of at least about 200, 210, 220, 230, 240, 250, 260, 270, 280, 290 or 300 degrees Celsius. In certain embodiments, the tobacco material, the wetted or wet tobacco material or the mixture comprising the tobacco material is heated for at least about 15 minutes to a temperature of at least about 200, 210, 220, 230, 240, 250, 260, 270, 280, 290 or 300 degrees Celsius. In certain embodiments, the tobacco material, the wetted or wet tobacco material or the mixture comprising the tobacco material is heated for at least about 20 minutes to a temperature of at least about 200, 210, 220, 230, 240, 250, 260, 270, 280, 290 or 300 degrees Celsius. In certain embodiments, the tobacco material, the wetted or wet tobacco material or the mixture comprising the tobacco material is heated for at least about 30 minutes to a temperature of at least about 200, 210, 220, 230, 240, 250, 260, 270, 280, 290 or 300 degrees Celsius. In certain embodiments, the tobacco material, the wetted or wet tobacco material or the mixture comprising the tobacco material is heated for at least about 60 minutes to a temperature of at least about 200, 210, 220, 230, 240, 250, 260, 270, 280, 290 or 300 degrees Celsius. The temperature to which the tobacco material, the wetted or wet tobacco material or the mixture comprising the tobacco material is heated to can be within a range of from about 200 to 300 degrees Celsius, about 200 to 290 degrees Celsius, about 200 to 280 degrees Celsius, about 200 to 270 degrees Celsius, about 200 to 260 degrees Celsius, about 200 to 250 degrees Celsius, about 200 to 240 degrees Celsius, about 200 to 230 degrees Celsius, about 200 to 220 degrees Celsius, or about 200 to 210 degrees Celsius.

The tobacco material, the wetted or wet tobacco material or the mixture comprising the tobacco material is generally heated in the presence of water and/or steam—in the methods of the present disclosure. The tobacco material, the wetted or wet tobacco material or the mixture comprising the tobacco material can be generally heated in the presence of exclusively water and/or exclusively steam—in the methods of the present disclosure. Desirably, if steam alone is used then the tobacco material is in the form of wetted or wet tobacco material or in the form of a mixture. The heating step can occur under pressure which can cause the boiling point of the liquid to increase. In one embodiment, the heating step is performed under conditions that subject the tobacco material to steam, including pressurised steam. In another embodiment, the tobacco material is subjected to pressurised steam in a contained volume or vessel. Exemplary pressure levels are discussed herein. Pressurised saturated steam can be used. Saturated steam is steam that is in equilibrium with heated water at the same pressure. Pressurised saturated steam can be created and used in an autoclave. As will be well understood by the skilled person, autoclaves work by increasing the temperature in a sealed enclosure through the use of pressure. Water is introduced to help penetration of the heat as water transfers heat more efficiently than dry air. Generally the temperature needs to be increased to around 121 degrees Celsius or higher over a period of time. The pressure increase helps the temperature of the steam to increase it above its flash point (point of vaporisation). Steam in the form of superheated steam can also be used. Superheated steam is steam at a temperature that is higher than its vaporisation (boiling) point at the absolute pressure where the temperature measurement is taken. The use of superheated steam can be achieved by using a superheated steam dryer.

Following the heating and optional pressure step, the tobacco material can optionally be washed with a second aqueous solution or solvent in a post-washing step. The second aqueous solution or solvent can be the same or different to the first aqueous solution or solvent used in the pre-washing step and/or the same or different to the liquid used in the heating/pressure steps. In certain embodiments, the second aqueous solution is a non-toxic aqueous solution containing water. In certain embodiments, the second aqueous solution is a buffer or a non-toxic aqueous solution containing the buffer. If a buffer is used then it will be at a desirable pH—such as at least about pH 6.0 or pH 7.0 or more. The second aqueous solution or solvent when combined with the tobacco material can be, for example, a 5% (w/v), 10% (w/v), 15% (w/v), 20% (w/v), 25% (w/v), 30% (w/v), 35% (w/v), 40% (w/v) or 45% (w/v) or more mixture. In certain embodiments a mixture of ratio 1:5 or 1:10 tobacco material: aqueous solution or solvent is used. In certain embodiments, the post-washing step is carried out for at least about 5, 10, 15, 20, 25, 30, 35, 40, 45, 50, 55, 60, 90, 120, 150 or 180 minutes or more at room temperature. In certain embodiments, the post-washing step is carried out at about room temperature or even elevated temperatures—such as about 20 degrees Celsius, about 30 degrees Celsius, about 40 degrees Celsius, about 50 degrees Celsius, about 60 degrees Celsius, about 80 degrees Celsius, or about 90 degrees Celsius or higher. In certain embodiments, the post-washing step can be carried out in the presence of physical agitation and/or more stringent washing conditions. It is considered that more stringent washing conditions—such as higher temperature and/or rigorous physical agitation—could further reduce the total tobacco specific nitrosamine content.

In a further optional step, the processed or treated tobacco material obtained or obtainable using the methods described herein is dried. Suitable conditions for drying tobacco material are well known in the art and include, for example, a temperature of about 50 degrees Celsius for about 17 hours.

At any stage of this process, the tobacco specific nitrosamine content—such as at least the NNK content—can be measured. In one embodiment, one or more tobacco specific nitrosamines are measured at the start of the process and/or at the end of the process. In another embodiment, one or more tobacco specific nitrosamines are measured at the end of the process to check that the tobacco specific nitrosamine content is present in a required amount or concentration. In another embodiment, one or more tobacco specific nitrosamines are measured before and then after the heating step. Thus, the methods described herein may comprise another optional step of measuring one or more of the tobacco specific nitrosamines described herein. The methods may comprise a step of measuring one or more of the tobacco specific nitrosamines in their free and/or bound form. In one embodiment, at least the level or amount of NNK is measured. The levels of these compounds may be measured in tobacco material, in tobacco feedstock or in tobacco homogenate and the like. The levels of these one or more compounds may be measured following treatment using the methods described herein. The levels of these one or more compounds may be measured before treatment using the methods described herein, during treatment using the methods described herein or at the end of the treatment using the methods described herein. The levels of these compounds may even be measured intermittently during treatment using the methods described herein. The levels may be compared with for example, control tobacco material that has not been subjected to the methods described herein. Thus, the measurement step may optionally be accompanied by a comparison step to compare the levels of nitrosamine(s) in the tobacco. Various methods that are known in the art may be used for measuring the tobacco specific nitrosamines—such as liquid chromatography methods including ultra-performance liquid chromatography and mass spectrometry, including tandem mass spectrometry which is widely known in the art. In one embodiment, ultra performance liquid chromatography-tandem mass (UPLC-MS/MS) is used.

In a further aspect, there is provided a method of reducing the amount of one or more tobacco specific nitrosamines bound to an insoluble tobacco matrix in tobacco material comprising the steps of: (a) providing tobacco material comprising one or more tobacco specific nitrosamines bound to the insoluble tobacco matrix; (b) optionally combining the tobacco material with an first aqueous solution or solvent; and (c) heating the tobacco material for at least about 30 seconds to a temperature of greater than about 100 degrees Celsius in the presence of a liquid or steam to release at least a portion of the tobacco specific nitrosamine(s) from the insoluble tobacco matrix of the tobacco material; and (d) removing at least a portion of the released tobacco specific nitrosamine(s) from the tobacco material. In one embodiment, the tobacco material that is heated in step (c) is wetted or wet before heating. For example, the tobacco material can be in the form of an at least 5% (w/v) mixture. In one embodiment, step (c) comprises heating the aqueous solution or solvent containing the tobacco material from step (b). In another aspect, there is provided a method of reducing the amount of NNK bound to an insoluble tobacco matrix in tobacco material comprising the steps of: (a) providing tobacco material comprising NNK bound to the insoluble tobacco matrix; (b) optionally combining the tobacco material with a first aqueous solution or solvent; and (c) heating the tobacco material for at least about 30 seconds to a temperature of greater than about 100 degrees Celsius in the presence of a liquid or steam to release at least a portion of the tobacco specific nitrosamine(s) from the insoluble tobacco matrix of the tobacco material; and (c) removing at least a portion of the released tobacco specific nitrosamine(s) from the tobacco material. In one embodiment, the tobacco material that is heated in step (c) is wetted or wet before heating. For example, the tobacco material can be in the form of an at least 5% (w/v) mixture. In one embodiment, step (c) comprises heating the mixture containing the tobacco material from step (b).

In certain embodiments, the maximal rate of tobacco specific nitrosamine, for example NNK, release occurs within 30-60 minutes of heating the tobacco material. In certain embodiments at least around 10,000 ng/g NNK is released within about 30-60 minutes of heating the tobacco material or at least about 13,000 ng/g NNK is released within about 30-60 minutes of heating the tobacco material. In certain embodiments, the rate of release is increased at higher temperatures. For example, around 10,000 ng/g NNK can be released at 130 degrees Celsius within about 30-60 minutes of heating the tobacco material, whereas about 13,000 ng/g NNK can be released at 140 degrees Celsius within about 30-60 minutes of heating the tobacco material. The amount of NNK release can continue for more than about 4 hours at about 130 degrees Celsius and for more than about 8 hours at about 140 degrees Celsius.

A temperature-dependent reduction of total NNK, that is, free and bound NNK can be observed. For example, after about 1 hour at about 110 degrees Celsius the total NNK content in tobacco material can be about 3400 ng/g. After about 1 hour at 120 degrees Celsius the total NNK content can be about 2900 ng/g. After about 1 hour at 130 degrees Celsius the total NNK content can be about 2600 ng/g.

A temperature-dependent reduction of matrix-bound NNK can be observed. After about 1 hour at 110 degrees Celsius the matrix-bound NNK content can be about 2480 ng/g. After about 1 hour at 120 degrees Celsius the matrix-bound NNK content can be about 1520 ng/g. After about 1 hour at 130 degrees Celsius the matrix-bound NNK content can be about 810 ng/g.

The tobacco material may comprise additives that include, but are not limited to, one or more of the following components as well as combinations thereof: flavorants, organic and inorganic fillers (for example, grains, processed grains, puffed grains, maltodextrin, dextrose, calcium carbonate, calcium phosphate, corn starch, lactose, manitol, xylitol, sorbitol, finely divided cellulose, and the like), binders (for example, povidone, sodium carboxymethylcellulose and other modified cellulosic types of binders, sodium alginate, xanthan gum, starch-based binders, gum arabic, lecithin, and the like), colorants (for example, dyes and pigments, including caramel coloring and titanium dioxide, and the like), humectants (for example, glycerin, propylene glycol, and the like), oral care additives, preservatives (for example, potassium sorbate, and the like), syrups (for example, honey, high fructose corn syrup, and the like used as flavorants), and disintegration aids (for example, microcrystalline cellulose, croscarmellose sodium, crospovidone, sodium starch glycolate, pregelatinized corn starch, and the like). Such additives are known to those having skill in the art and may be present in amounts and in forms known in the art.

Without being bound by any particular theory, tobacco specific nitrosamines, in addition to their formation during curing, are understood to be formed during the processing of tobacco. Therefore, the methods described herein may be particularly efficient for reducing the level, amount or concentration of one or more of tobacco specific nitrosamines—such as NNK—that are generated in a tobacco product, including tobacco products prepared from cured tobacco or a tobacco slurry in which high tobacco specific nitrosamine levels may accumulate. As discussed herein, the methods described herein may be particularly suitable for the preparation of reconstituted tobacco.

In a further aspect, there is provided a (processed or treated) tobacco material comprising less than about 2400 ng/g NNK in the insoluble tobacco matrix and at least about 900 ng/g free NNK. In certain embodiments, the (processed or treated) tobacco material comprises less than about 2480 ng/g NNK in the insoluble tobacco matrix and at least about 930 ng/g free NNK. In certain embodiments, the (processed or treated) tobacco material comprises less than about 2481 ng/g NNK in the insoluble tobacco matrix and at least about 934 ng/g free NNK. In certain embodiments, the (processed or treated) tobacco material comprises less than about 1550 ng/g NNK in the insoluble tobacco matrix and at least about 1300 ng/g free NNK. In certain embodiments, the (processed or treated) tobacco material comprises less than about 1520 ng/g NNK in the insoluble tobacco matrix and at least about 1390 ng/g free NNK. In certain embodiments, the (processed or treated) tobacco material comprises less than about 1520 ng/g NNK in the insoluble tobacco matrix and at least about 1397 ng/g free NNK. In certain embodiments, the (processed or treated) tobacco material comprises less than about 810 ng/g NNK in the insoluble tobacco matrix and at least about 1800 ng/g free NNK. In certain embodiments, the (processed or treated) tobacco material comprises less than about 809 ng/g NNK in the insoluble tobacco matrix and at least about 1850 ng/g free NNK. In certain embodiments, the (processed or treated) tobacco material comprises less than about 809 ng/g NNK in the insoluble tobacco matrix and at least about 1859 or 1860 ng/g free NNK.

In certain embodiments, the (processed or treated) tobacco material comprises between about 2500 ng/g NNK and 800 ng/g NNK in the insoluble tobacco matrix and between about 900 ng/g and 1900 ng/g free NNK. In certain embodiments, the (processed or treated) tobacco material comprises between about 2480 ng/g NNK and 810 ng/g NNK in the insoluble tobacco matrix and between about 930 ng/g and 1860 ng/g free NNK. In certain embodiments, the (processed or treated) tobacco material comprises between about 2481 ng/g NNK and 809 ng/g NNK in the insoluble tobacco matrix and between about 934 ng/g and 1859 ng/g free NNK.

The tobacco material obtained or obtainable by the methods described herein may be incorporated into various consumable products—such as tobacco products. Also described herein are tobacco products formed from the tobacco material obtained or obtainable by the methods described herein. Also encompassed by this disclosure are methods for making such tobacco products. Tobacco products include without limitation smoking articles or smokable articles and smokeless tobacco products, including non-combustible products, heated products, and aerosol-generating products. Non-limiting examples of smoking or smokable articles include cigarettes, cigarillos, cigars and pipe tobaccos. Non-limiting examples of smokeless tobacco products include chewing tobaccos, snuffs, and substrates for use in aerosol-generating products. Smokeless tobacco products may comprise tobacco in any form, including as dried particles, shreds, granules, powders, or a slurry, deposited on, mixed in, surrounded by, or otherwise combined with other ingredients in any format, such as flakes, films, tabs, foams, or beads. Liquid contents of smokeless tobacco products can be contained in a device or enclosed in a form, such as beads, to preclude interaction with a water-soluble wrapper. The wrapper may be shaped as a pouch to partially or completely enclose tobacco-incorporating compositions, or to function as an adhesive to hold together a plurality of tabs, beads, or flakes of tobacco. Exemplary materials for constructing a wrapper include film compositions comprising HPMC, CMC, pectin, alginates, pullulan, and other commercially viable, edible film-forming polymers. Other wrapping materials may include pre-formed capsules produced from gelatin, HPMC, starch/carrageenan, or other commercially available materials. Such wrapping materials may include tobacco as an ingredient. Wrappers that are not orally disintegrable may be composed of woven or nonwoven fabrics, of coated or uncoated paper, or of perforated or otherwise porous plastic films. Wrappers may incorporate flavouring or colouring agents. Smokeless products can be assembled together with a wrapper utilizing any method known to persons skilled in the art of commercial packaging, including methods such as blister packing, in which a small package can be formed by a vertical form/fill/seal packaging machine.

One aspect relates to a method for producing an aerosol from tobacco material comprising the steps of: (a) providing the tobacco material obtained or obtainable by the methods described herein; and (b) heating the tobacco material to produce an aerosol. Another aspect relates to a method for reducing the amount or concentration of one or more tobacco specific nitrosamines—such as NNK—in an aerosol. Generally, the aerosol will be in the form of smoke. The method comprises the steps of: (a) providing tobacco material comprising one or more tobacco specific nitrosamines; (b) heating the tobacco material for at least about 30 seconds to a temperature of greater than about 100 degrees Celsius in the presence of a liquid or steam to release at least a portion of the tobacco specific nitrosamine(s) from the insoluble tobacco matrix of the tobacco material; (c) removing at least a portion of the released tobacco specific nitrosamine(s) from the tobacco material; and (d) heating the tobacco material from step (c) to produce an aerosol. An aerosol obtained or obtainable by the methods described herein is also provided. Suitably, the aerosol that is obtained has a lower level of NNK as compared to an aerosol from a control tobacco material that has not been subjected to at least step (b). The tobacco material obtained or obtainable by the methods described herein may be formed into reconstituted tobacco. Reconstituted tobacco can generally be formed in a variety of ways. For instance, in one embodiment, band casting can be utilised to form the reconstituted tobacco. Band casting typically employs a slurry of finely divided tobacco parts and a binder that is coated onto a steel band and then dried. After drying, the sheet is blended with natural tobacco strips or shredded and used in various tobacco products, including as a cigarette filler. Some examples of processes for producing reconstituted tobacco are described in U.S. Pat. Nos. 3,353,541, 3,420,241, 3,386,449, 3,760,815 and 4,674,519. Reconstituted tobacco can also be formed by a papermaking process. Some examples of processes for forming reconstituted tobacco according to this process are described in U.S. Pat. Nos. 3,428,053, 3,415,253, 3,561,451, 3,467,109, 3,483,874, 3,860,012, 3,847,164, 4,182,349, 5,715,844, 5,724,998; and 5,765,570. For example, the formation of reconstituted tobacco using papermaking techniques can involve the steps of mixing tobacco with water, extracting the soluble ingredients therefrom, concentrating the soluble ingredients, refining the tobacco, forming a web, reapplying the concentrated soluble ingredients, drying, and threshing. Various ingredients—such as flavour or colour treatments—can be applied to the web. Thus, according to a further aspect, there is provided a method of preparing reconstituted tobacco comprising the steps of: (a) providing tobacco material comprising one or more tobacco specific nitrosamines; (b) heating the tobacco material for at least about 30 seconds to a temperature of greater than about 100 degrees Celsius; and (c) manufacturing the tobacco material obtained from step (b) into reconstituted tobacco. Suitably, the reconstituted tobacco is prepared by a band casting process or a papermaking process. The tobacco material can optionally be washed before and/or after the heating step.

According to another embodiment, the tobacco material obtained or obtainable by the methods described herein may be formed into a tobacco sheet—such as a reconstituted tobacco sheet. According to this embodiment, the method may comprise the steps of: (a) obtaining (treated or processed) tobacco material—such as a tobacco homogenate—according to the methods described herein; (b) preparing a slurry of tobacco homogenate; (c) casting the slurry of the tobacco homogenate; and (d) drying the slurry of the tobacco homogenate to form a reconstituted tobacco sheet.

According to another embodiment, the method may comprise the steps of: (a) obtaining (treated or processed) tobacco material—such as a tobacco homogenate—according to the methods described herein and preparing a tobacco slurry; (b) casting the slurry of the tobacco homogenate; and (c) drying the slurry of the tobacco homogenate to form a tobacco sheet.

The step of casting the slurry of the tobacco homogenate may be performed using any of the casting or paper making processes that are known in the art. By way of example, casting processes are described in U.S. Pat. Nos. 5,724,998 and 5,584,306; paper-making processes are described in U.S. Pat. Nos. 4,341,228; 5,584,306 and 6,216,706. Casting processes typically include casting the slurry onto a continuous stainless steel belt, drying the cast slurry to form a reconstituted tobacco sheet and removing said sheet. Papermaking processes typically include casting the aqueous slurry from a head box onto a wire screen for forming the desired sheet. The aqueous slurry may be separated into a soluble portion and a fibrous portion. Water is drained from the fibrous portion and a sheet is so-formed is subsequently treated and dried.

The tobacco slurries may further comprise one or more binders—such as gums and pectins. As described above, tobacco slurries that are used to prepare reconstituted tobacco sheets may further comprise common additives that include, but are not limited to, one or more of the following components as well as combinations of these: wood cellulose fibers, aerosol formers, sugars, and flavourants and binders. Additives of the list described above are known to those having skill in the art and may be present in these aqueous slurries in amounts and in forms known in the art.

Once prepared, the reconstituted tobacco sheets described herein may be cut in a similar fashion as whole leaf tobacco to produce tobacco filler suitable for cigarettes and other tobacco products. The reconstituted tobacco sheets described herein may be further trashed or flayed with mechanical fingers into sized pieces similar to natural tobacco lamina strips or cut into diamond shaped pieces, between about 50 to 100 mm on a side. The reconstituted tobacco sheet pieces described herein may be further blended with other tobaccos such as flue-cured tobacco, Burley tobacco, Maryland tobacco, Oriental tobacco, rare tobacco, specialty tobacco, expanded tobacco and the like. The precise amount of each type of tobacco within a tobacco blend used for the manufacture of a particular cigarette brand varies from brand to brand. See, for example, Tobacco Encyclopaedia, Voges (Ed.) p. 44-45 (1984), Browne, The Design of Cigarettes, 3rd Ed., p. 43 (1990) and Tobacco Production, Chemistry and Technology, Davis et al. (Eds.) p. 346 (1999). The entire blend may then be shredded into a cut filler and incorporated into a tobacco product. Accordingly, methods are provided for making a tobacco product comprising tobacco (for example, reconstituted tobacco sheet) with reduced amounts of tobacco specific nitrosamines—such as NNK.

The tobacco material obtained or obtainable according to the disclosure herein can also be used in tobacco cut filler and in a smoking article formed from a tobacco rod of the cut filler. Conventionally, cut filler tobacco products for smoking articles are formed predominantly from the lamina portion of the tobacco leaf, which is separated from the stem portion of the leaf during a threshing process. Much of the stem portion that remains after the lamina has been removed and separated is not used. In order to increase the amount of the tobacco material that can be used commercially, some tobacco stems can be added back into the cut filler together with the lamina. In order to improve the taste and burning characteristics of the tobacco stem for use in the cut filler, the stems are often first subjected to one or more treatment procedures, which can include the procedures described herein. The rolling step can be carried out on tobacco stems that have been subjected to the method of the present disclosure. The stems can be rolled to a desired thickness—such as a mean thickness of about 0.6 mm to 0.8 mm. During subsequent processing and storage steps, the stems can expand to a final thickness of about 0.8 mm to about 1.0 mm. After rolling, the stems are dried and transferred to the tobacco production plant, where they are cut and added to the tobacco cut filler. In some cases, the rolling step may alternatively be incorporated as part of the on-line production process for cut filler. Typically the moisture content of the tobacco stems is about 28% to about 34% oven volatiles prior to rolling in order to prevent damage to the structure of the stems. If necessary, the tobacco stems can be conditioned prior to rolling in order to increase the moisture content to this level. Known processes for conditioning tobacco stems involve contacting the stems with water, steam or a mixture of water and steam. In methods where the rolling step is incorporated on-line and dried stems are used, the conditioning step will typically take longer and may require a soaking step in which the stems are soaked in water for a number of hours prior to rolling. The tobacco stems can be rolled using a one step rolling process to reduce the thickness of the stems to the desired mean thickness. After rolling, the stems can be cut to a cut width of between 0.1 mm and 0.2 mm. The cut rolled stems are then optionally expanded using known stem expansion techniques, and then dried. Where the stems are pre-rolled and dried, it will typically be necessary to condition the stems prior to cutting in order to increase the moisture content of the tobacco stems back to between 28% and 34% oven volatiles. This increases the pliability of the tobacco stems in order to limit damage or breakage of the stems during cutting. Finally, the cut rolled stems are combined with tobacco cut lamina and any additional tobacco materials in order to form cut filler having at least 5% by weight of the cut rolled tobacco stems. Thus, in a further aspect, there is provided a method for preparing tobacco for use as a tobacco cut filler comprising the steps of: (a) providing tobacco material comprising one or more tobacco specific nitrosamines; (b) heating the tobacco material for at least about 30 seconds to a temperature of greater than about 100 degrees Celsius in the presence of a liquid or steam to release at least a portion of the tobacco specific nitrosamine(s) from the insoluble tobacco matrix of the tobacco material; (c) removing at least a portion of the released tobacco specific nitrosamine(s) from the tobacco material; (d) washing the tobacco material from step (c) with an aqueous solution or solvent to release the tobacco specific nitrosamine(s) from the tobacco material; and (e) rolling and cutting the tobacco material. There is also described a method of treating tobacco material—such as tobacco stems—for use in tobacco cut filler, the method comprising the steps of: (a) providing tobacco material comprising one or more tobacco specific nitrosamines; (b) heating the tobacco material for at least about 30 seconds to a temperature of greater than about 100 degrees Celsius in the presence of a liquid or steam to release at least a portion of the tobacco specific nitrosamine(s) from the insoluble tobacco matrix of the tobacco material; (c) removing at least a portion of the released tobacco specific nitrosamine(s) from the tobacco material; (d) washing the tobacco material from step (c) with an aqueous solution or solvent to release the tobacco specific nitrosamine(s) from the tobacco material; (e) rolling the tobacco material; (f) cutting the re-tobacco material; and (g) optionally drying the cut rolled stems. The rolled tobacco stems can be combined with tobacco lamina such that the steps are carried out on the combined tobacco stems and lamina. The cutting step can comprise cutting the rolled stems to a cut width of between about 0.3 mm and 1.3 mm. The method can comprise the steps of: removing stems from the tobacco leaf; cutting the stems to an average length of between about 15 mm and 80 mm; and rolling the stems to a thickness of between 0.1 mm and 0.5 mm. A method of producing cut filler comprising rolled tobacco stems is also provided, the method comprising: treating tobacco stems using the method described herein; and blending the treated stems with at least one type of tobacco lamina, expanded tobacco or reconstituted tobacco to produce cut filler.

The tobacco cut filler obtained or obtainable by this method can comprise at least 60%, and preferably at least 80% by weight tobacco lamina having a mean cut width between 0.8 mm and 1.1 mm, suitably, about 0.9 mm, and a mean thickness of about 0.2 mm. The tobacco cut filler can comprise up to 95% by weight tobacco lamina with a mean cut width between about 0.8 mm and 1.1 mm, more suitably about 0.9 mm, and a mean thickness of about 0.2 mm. The particles of tobacco lamina in the cut filler are therefore of similar dimensions to the particles of tobacco stem. As such, the tobacco stems are not visually distinct from the tobacco lamina, even at a high inclusion rate. In addition, the blend of tobacco stems and lamina can advantageously be transported and processed effectively without significant settling of the stems. Suitably, the mean cut width of the cut rolled tobacco stems is within about 0.1 mm, more suitably within about 0.05 mm of the mean thickness of the tobacco lamina in the cut filler. Cut fillers may be incorporated into a variety of smoking articles. For example, the cut filler may be used in the tobacco rod of a combustible smoking article, such as a filter cigarette, cigarillo or cigar. Alternatively, the cut filler may be used to provide the tobacco aerosol generating substrate in a distillation based smoking article, or an electrically heated smoking system. Alternatively, the cut filler may be used as a roll-your-own product, or loose tobacco product for example, for use in a pipe.

The tobacco material may be derived from a naturally occurring tobacco plant, a mutant tobacco plant, a non-naturally occurring tobacco plant or a transgenic tobacco plant.

The tobacco material can be derived or derivable from tobacco plants, which include plants of the genus *Nicotiana*, various species of *Nicotiana*, including *N. rustica* and *N. tabacum*. The tobacco material can be derived from varieties of *Nicotiana* species, commonly known as flue or bright varieties, Burley varieties, dark varieties and oriental/Turkish varieties. In some embodiments, the tobacco material is derived from a Burley, Virginia, flue-cured, air-cured, fire-cured, Oriental, or a dark tobacco plant. In some embodiments, the tobacco material is derived, for example, from one or more of the following varieties: *N. tabacum* AA 37-1, *N. tabacum* B 13P, *N. tabacum* Xanthi (Mitchell-Mor), *N. tabacum* KT D#3 Hybrid 107, *N. tabacum* Bel-W3, *N. tabacum* 79-615, *N. tabacum* Samsun Holmes NN, F4 from cross *N. tabacum* BU21×*N. tabacum* Hoja Parado, line 97, *N. tabacum* KTRDC#2 Hybrid 49, *N. tabacum* KTRDC#4 Hybrid 1 10, *N. tabacum* Burley 21, *N. tabacum* PM016, *N. tabacum* KTRDC#5 KY 160 SI, *N. tabacum* KTRDC#7 FCA, *N. tabacum* KTRDC#6 TN 86 SI, *N. tabacum* PMO21, *N. tabacum* K 149, *N. tabacum* K 326, *N. tabacum* K 346, *N. tabacum* K 358, *N. tabacum* K 394, *N. tabacum* K 399, *N. tabacum* K 730, *N. tabacum* KY 10, *N. tabacum* KY 14, *N. tabacum* KY 160, *N. tabacum* KY 17, *N. tabacum* KY 8959, *N. tabacum* KY 9, *N. tabacum* KY 907, *N. tabacum* MD 609, *N. tabacum* McNair 373, *N. tabacum* NC 2000, *N. tabacum* PG 01, *N. tabacum* PG 04, *N. tabacum* P01, *N. tabacum* P02, *N. tabacum* P03, *N. tabacum* RG 11, *N. tabacum* RG 17, *N. tabacum* RG 8, *N. tabacum* Speight G-28, *N. tabacum* TN 86, *N. tabacum* TN 90, *N. tabacum* VA 509, *N. tabacum* AS44, *N. tabacum* Banket A1, *N. tabacum* Basma Drama B84/31, *N. tabacum* Basma I Zichna ZP4/B, *N. tabacum* Basma Xanthi BX 2A, *N. tabacum* Batek, *N. tabacum* Besuki Jember, *N. tabacum* C104, *N. tabacum* Coker 319, *N. tabacum* Coker 347, *N. tabacum* Criollo Misionero, *N. tabacum* PM092, *N. tabacum* Delcrest, *N. tabacum* Djebel 81, *N. tabacum* DVH 405, *N. tabacum* Galpao Comum, *N. tabacum* HB04P, *N. tabacum* Hicks Broadleaf, *N. tabacum* Kabakulak Elassona, *N. tabacum* PM102, *N. tabacum* Kutsage E1, *N. tabacum* KY 14xL8, *N. tabacum* KY 171, *N. tabacum* LA BU 21, *N. tabacum* McNair 944, *N. tabacum* NC 2326, *N. tabacum* NC 71, *N. tabacum* NC 297, *N. tabacum* NC 3, *N. tabacum* PVH 03, *N. tabacum* PVH 09, *N. tabacum* PVH 19, *N. tabacum* PVH 2110, *N. tabacum* Red Russian, *N. tabacum* Samsun, *N. tabacum* Saplak, *N. tabacum* Simmaba, *N. tabacum* Talgar 28, *N. tabacum* PM132, *N. tabacum* Wislica, *N. tabacum* Yayaldag, *N. tabacum* NC 4, *N. tabacum* TR Madole, *N. tabacum* Prilep HC-72, *N. tabacum* Prilep P23, *N. tabacum* Prilep PB 156/1, *N. tabacum* Prilep P12-2/1, *N. tabacum* Yaka JK-48, *N. tabacum* Yaka JB 125/3, *N. tabacum* TI-1068, *N. tabacum* KDH-960, *N. tabacum* TI-1070, *N. tabacum* TW136, *N. tabacum* PM204, *N. tabacum* PM205, *N. tabacum* Basma, *N. tabacum* TKF 4028, *N. tabacum* L8, *N. tabacum* TKF 2002, *N. tabacum* TN90, *N. tabacum* GR141, *N. tabacum* Basma xanthi, *N. tabacum* GR149, *N. tabacum* GR153, and *N. tabacum* Petit Havana.

Further aspects of the present disclosure are set forth in the following paragraphs.

1. A method of reducing the amount of one or more tobacco specific nitrosamines in tobacco material comprising the steps of: (a) providing tobacco material comprising one or more tobacco specific nitrosamines; (b) heating the tobacco material for at least about 30 seconds to a temperature of greater than about 100 degrees Celsius in the presence of a liquid or steam to release at least a portion of the one or more tobacco specific nitrosamines from the insoluble tobacco matrix of the tobacco material; and (c) removing at least a portion of the released tobacco specific nitrosamine(s) from the tobacco material.
2. The method according to paragraph 1, wherein the tobacco specific nitrosamine(s) comprises, consists or consists essentially of NNK.
3. The method according to paragraph 1 or paragraph 2, wherein the tobacco material provided in step (a) is contacted with a first aqueous solution or solvent prior to step (b).
4. The method according to any of the preceding paragraphs, wherein the tobacco specific nitrosamine(s) is removed from the sample by one or more washes with a second aqueous solution or solvent.

5. The method according to paragraph 3 or paragraph 4, wherein in the first and/or second aqueous solution or solvent is the same of different.
6. The method according to any of the preceding paragraphs, wherein the tobacco material is selected from the group consisting of: tobacco leaf and/or tobacco stems and/or tobacco dust and/or tobacco leaf prime lamina strip or a combination of two or more thereof.
7. The method according to any of the preceding paragraphs, wherein the tobacco material is heated in the presence of water or steam produced from water.
8. The method according to any of the preceding paragraphs, wherein the tobacco material is heated in step (b) in the presence of pressurised steam and/or superheated steam.
9. Tobacco material obtained or obtainable by the method of any of paragraphs 1 to 8.
10. A tobacco material comprising less than about 2400 ng/g NNK in the insoluble tobacco matrix and at least about 900 ng/g free NNK.
11. A method for reducing the amount or concentration of one or more tobacco specific nitrosamines in an aerosol comprising the steps of: (a) providing tobacco material comprising one or more tobacco specific nitrosamines; (b) heating the tobacco material for at least about 30 seconds to a temperature of greater than about 100 degrees Celsius in the presence of a liquid or steam to release at least a portion of the one or more tobacco specific nitrosamines from the insoluble tobacco matrix of the tobacco material; (c) removing at least a portion of the released tobacco specific nitrosamine(s) from the tobacco material; and (d) heating the tobacco material from step (b) to produce an aerosol.
12. A method for producing reconstituted tobacco comprising the steps of: (a) providing tobacco material comprising one or more tobacco specific nitrosamines; (b) heating the tobacco material for at least about 30 seconds to a temperature of greater than about 100 degrees Celsius; (c) washing the tobacco material from step (b) with an aqueous solution or solvent to release the tobacco specific nitrosamine(s) from the tobacco material; (d) manufacturing the tobacco material obtained from step (c) into reconstituted tobacco; and (e) optionally incorporating the reconstituted tobacco into a tobacco product.
13. A method for producing reconstituted tobacco comprising the steps of: (a) providing tobacco material comprising one or more tobacco specific nitrosamines; (b) manufacturing said tobacco material into reconstituted tobacco by separating tobacco fibres from soluble material; (c) heating the separated fibres for at least about 30 seconds to a temperature of at least 100 degrees Celsius in the presence of a liquid or steam to release at least a portion of the tobacco specific nitrosamine(s) from the insoluble tobacco matrix of the separated fibres; (d) washing the fibres with an aqueous solution or solvent; (e) recombining the fibres and soluble material to form a reconstituted tobacco sheet; and (f) optionally incorporating the reconstituted tobacco into a tobacco product.
14. A method for preparing tobacco for use as a tobacco cut filler comprising the steps of: (a) providing tobacco material—such as a to tobacco stems—comprising one or more tobacco specific nitrosamines; (b) heating the tobacco material for at least about 30 seconds to a temperature of greater than about 100 degrees Celsius in the presence of a liquid or steam to release at least a portion of the tobacco specific nitrosamine(s) from the insoluble tobacco matrix of the tobacco material; (c) removing at least a portion of the released tobacco specific nitrosamine(s) from the tobacco material; and (d) rolling and cutting the tobacco material.
15. A method of producing cut filler comprising rolled tobacco stems comprising the steps of: (a) providing tobacco stems comprising one or more tobacco specific nitrosamines; (b) heating the tobacco stems for at least about 30 seconds to a temperature of greater than about 100 degrees Celsius in the presence of a liquid or steam to release at least a portion of the tobacco specific nitrosamine(s) from the insoluble tobacco matrix of the tobacco stems; (c) removing at least a portion of the released tobacco specific nitrosamine(s) from the tobacco stems; (d) blending the treated stems with at least one type of tobacco lamina, expanded tobacco or reconstituted tobacco; and (e) producing cut filler.

The following examples are provided as an illustration and not as a limitation. Unless otherwise indicated, the present invention employs conventional techniques and methods of molecular biology and plant biology.

EXAMPLES

Example 1

Method for Analysis of Free and Bound NNK in Tobacco

Aliquots of tobacco samples (for example, about 750 mg) are extracted with about 30 mL of Tris-HCl buffer (50 mM; pH 7.4) by shaking for about one hour at approximately room temperature. Internals standard (100 ng/mL NNK-$d_4$) are added. Samples (0.4 mL) of the extracts are filtered using a 0.2 μM filter and the NNK content is analysed using ultra performance liquid chromatography-tandem mass (UPLC-MS/MS). The sample concentrations calculated from these extract concentrations correspond to the "free NNK" concentrations in the sample. After treating the extraction mixtures (for example, by heating to about 130° C. for about 4 hours) and filtering aliquots of the extracts, NNK concentrations are again measured by UPLC-MS/MS. From these values, the "total NNK" concentration in the samples can be calculated. The "bound NNK" concentration is the difference between the "total NNK" and the "free NNK" concentrations.

An alternative method for "total-NNK" extraction comprises acidification of the extraction mixtures with concentrated HCl (for example, 3 mL of 37% HCl added to 30 mL) and incubation for 48 hours at 80° C. The acidic extracts are neutralised before filtration and UPLC analysis by adding NaOH solution (6N, 40 μL) and magnesium hydroxide suspension (10%; 40 μL) to 320 μL of extract.

Example 2

UPLC Analysis

The column used is Waters Acquity BEH C18, 1.7 μm, 2.1×50 mm. The eluents used are: (A) ammonium bicarbonate (10 mM; adjusted to pH 9.8 with ammonia)+2% (v/v) acetonitrile; (B) acetonitrile. The gradient used is 0 min—5% B; 0.5 min—5% B; 3.3 min—18.3% B. The flow that is used is 0.5 mL/min. The column temperature that is used is 50° C.

Example 3

MS/MS Methodology

This analysis is carried out on a Waters TQ spectrometer using the following MRM transitions: NNK: 208.2→122.2; dwell time 100 ms; NNK-d4: 212.2→126.2; dwell time 100 ms; Capillary voltage: 0.6 kV; Cone voltage: 25 V; Collision energy: 11 eV; Source temperature: 120° C.; Desolvation temperature: 400° C.; Desolvation gas flow: 800 L/h.

Example 4

Analysis of Free and Matrix-Bound NNK in Tobacco Samples

Making use of the finding that matrix-bound NNK is released by extraction with 1N HCl (at 80° C. for two days) free and matrix-bound NNK is analysed in tobacco samples using UPLC-MS/MS as described above. By applying this method it is found that a large proportion of NNK in Burley leaves, Burley stems and reconstituted tobacco is present in the matrix-bound form.

As shown in FIG. 1 the highest total NNK content in this analysis was found in the reconstituted tobacco and in Burley stems. The total free NNK content and the total bound NNK was highest in the reconstituted tobacco and in Burley stems.

Example 5

Release of Matrix-Bound NNK from Water Washed Burley Stem

The above mentioned acidic (or alkaline) release of matrix-bound NNK cannot generally be used for NNK removal from tobacco material intended for human use, because of its effect on the physical integrity of the tobacco. Therefore, other methods are required.

Figure 2:
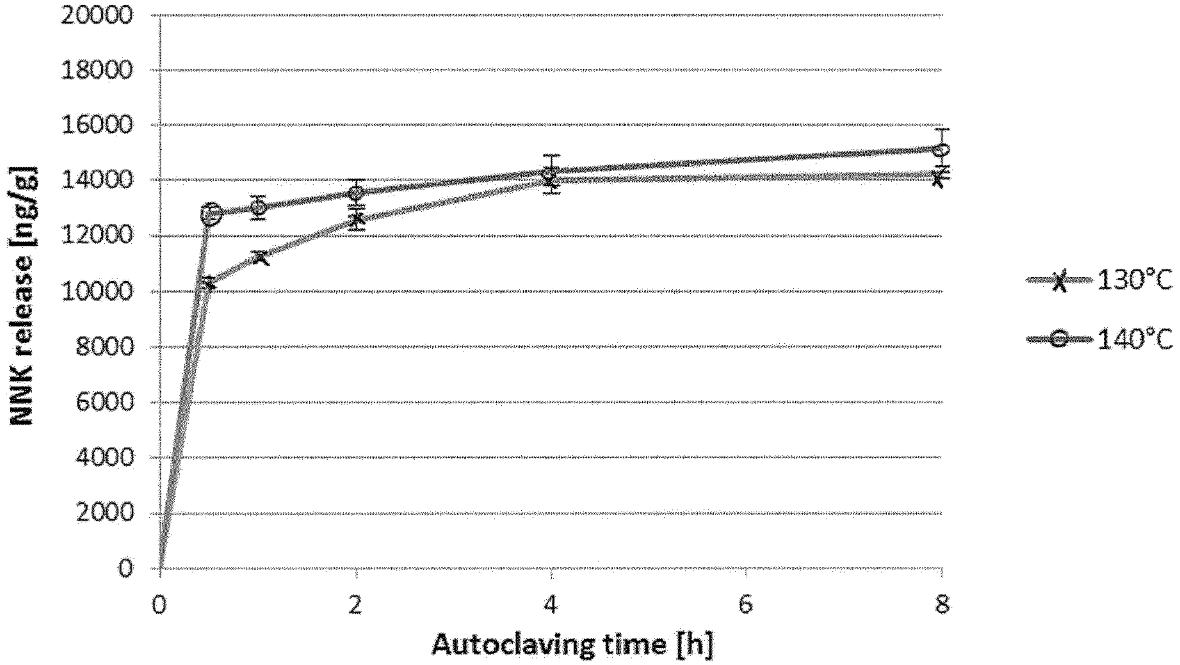
FIG. 2 shows the release of NNK by autoclaving from water-washed Burley stem according to one of the embodiment of this disclosure.

Water-washed Burley stems are heated in water to 130° C. or 140° C. in a laboratory autoclave. This releases a significant amount of matrix-bound NNK within four hours. As can be seen in FIG. 2, the maximal rate of NNK release in Burley stems occurred within the first 30-60 minutes with around 10,000 ng/g being released at 130 degrees Celsius and about 13,000 ng/g being released at 140 degrees Celsius. The amount of NNK release continued for up to about 4 hours at 130 degrees Celsius and for up to about 8 hours at 140 degrees Celsius.

Figure 3:
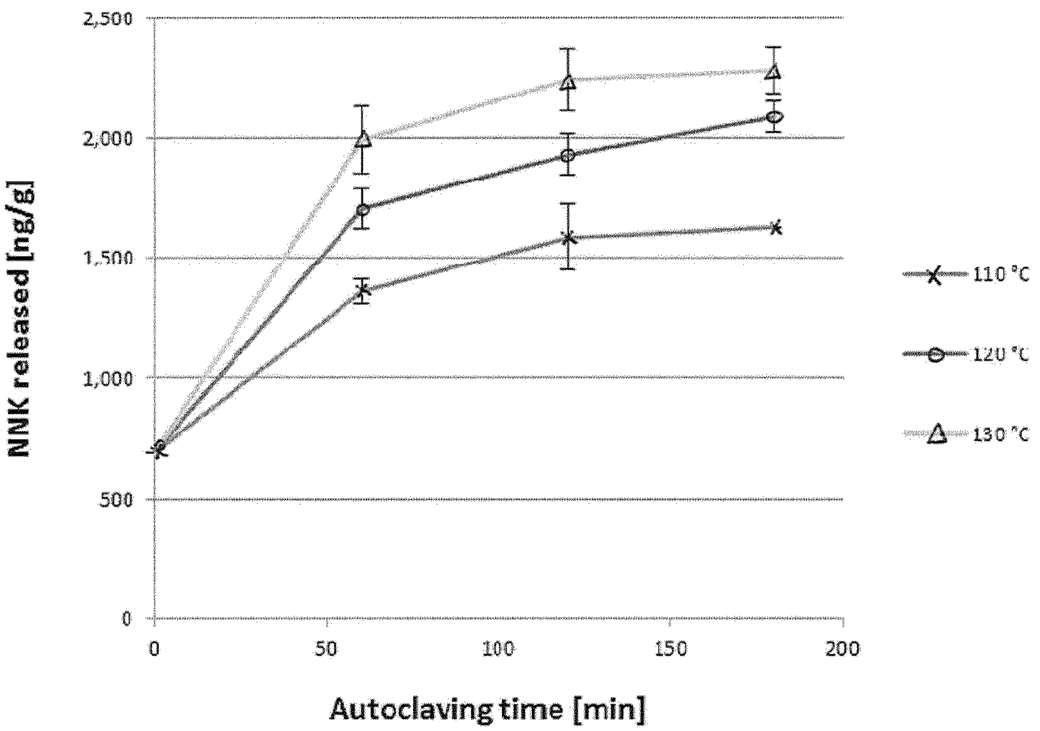
FIG. 3 shows the release of NNK by autoclaving from 3R4F filler according to one of the embodiment of this disclosure.

The same overall effect is observed for filler from 3R4F experimental cigarettes extracted in water at temperatures from 110° C. to 130° C. A clear temperature dependence of the rate of NNK release is observed. As can be seen in FIG. 3, a rapid rate of release of NNK occurred within the first 60 minutes with about 1,400 ng/g, 1,700 ng/g and 2,000 ng/g being released at 110 degrees Celsius, 120 degrees Celsius and 130 degrees Celsius, respectively. After about 60 minutes the rate of release decreased although a continued release of NNK was still observed after about 200 minutes.

Example 6

Removal of Matrix-Bound NNK from Burley Stems

The potential of the method described herein for the removal of matrix-bound NNK from tobacco materials is assessed by applying a three-step washing/autoclaving/washing procedure on tobacco specific nitrosamines-rich Burley stems. The stems are first washed with water (1.5 L for 100 g stems) for about two hours at about room temperature; then the wet stems are autoclaved and washed again with water for about two hours. After this treatment the material is dried (about 50° C. for about 17 h) and analysed for both free and matrix-bound NNK content. The results are shown in Table 1 and FIG. 4.

Figure 4:
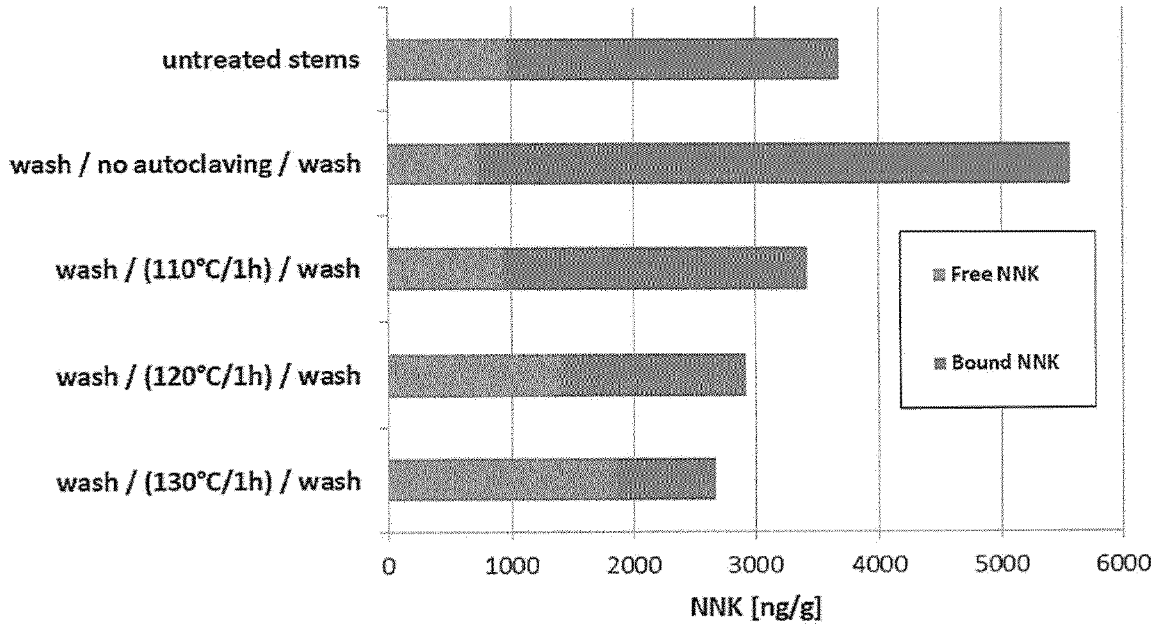
FIG. 4 shows the effect of autoclaving and washing on free and bound NNK in Burley stems according to one of the embodiment of this disclosure.

As shown in FIG. 4, a temperature-dependent reduction of total NNK (=free+bound NNK) is observed. The 1 hr at 110 degrees Celsius method resulted in total NNK content of about 3415 ng/g. The 1 hr at 120 degrees Celsius method resulted in total NNK content of about 2917 ng/g. The 1 hr at 130 degrees Celsius method resulted in total NNK content of about 2668 ng/g. In comparison, the total NNK content in untreated stems was about 3680 ng/g. In the no-autoclaving method, the total NNK content was about 5024 ng/g. As also shown in FIG. 4, a strong temperature-dependent reduction of matrix-bound NNK is observed. The 1 hr at 110 degrees Celsius method resulted in a matrix-bound NNK content of about 2481 ng/g. The 1 hr at 120 degrees Celsius method resulted in a matrix-bound NNK content of about 1520 ng/g. The 1 hr at 130 degrees Celsius method resulted in a matrix-bound NNK content of about 809 ng/g. In comparison, the matrix-bound NNK content in untreated stems was about 2715 ng/g. In the no-autoclaving method, the matrix-bound NNK content was about 4848 ng/g.

As also shown in FIG. 4, a strong temperature-dependent increase of free NNK is observed. The 1 hr at 110 degrees Celsius method resulted in a free NNK content of about 934 ng/g. The 1 hr at 120 degrees Celsius method resulted in a free NNK content of about 1397 ng/g. The 1 hr at 130 degrees Celsius method resulted in a free NNK content of about 1859 ng/g. In comparison, the matrix-bound content in untreated stems was about 2715 ng/g. In the no-autoclaving method, the matrix-bound content was about 4848 ng/g.

The higher bound-NNK content in the "no autoclaving" sample as compared to the untreated stems is believed to be attributed to the loss of water-solubles during the first washing step which accounts for ~30-40% of the dry weight in untreated stems. The large proportion of free NNK in the autoclaved stems indicates that the last washing step is not exhaustive and that a further reduction of the total NNK content could be achieved by applying an improved washing method, for example, with a more intense physical agitation of the water/stem mixture.

Example 7

Smoke NNK Analysis of Cigarettes with Added Water-Washed Burley Stem

The smoke of cigarettes with 20% added washed Burley stem or 20% autoclaved washed Burley stem material treated as described herein, is analysed in order to demonstrate that matrix-bound NNK released during autoclaving contributes to smoke NNK.

Preparation of washed/autoclaved Burley stems: Shredded Burley stems are extracted three times sequentially with 1200 mL water (1 hour at 70° C.), each. After each extraction, the solids are separated by vacuum filtration. After the third extraction the solids are frozen and lyophilised. Then, the extracted stems are washed four times with MeOH/H2O (1:1; 480 mL each; centrifuged at 4000 rpm for 10 min after each step), twice with 480 mL water (same conditions) and then lyophilised again to give 47 g of washed Burley stem (wBS). A part of this wBS (20 g) is autoclaved in water (300 mL; 4 hours at 130° C.). Then, the mixture is centrifuged (10 min, 4000 rpm) and the sediment is washed three times with water (300 mL) centrifuging after each washing step. Freeze-drying the washed material gives 10.9 g of autoclaved washed Burley stem (aBS).

Cigarette preparation: Cigarettes are prepared by hand-rolling blends of a Burley cut-filler with wBS or aBS. The tobacco is conditioned before rolling for 1-2 h at 60-65% RH. 700 mg of tobacco is used per cigarette. Fifteen cigarettes are produced for each of the three sample types: cigarette A: 100% Burley cigarette; cigarette B: 80% Burley+20% wBS; and cigarette C: 80% Burley+20% aBS.

Smoke analysis: The cigarettes are smoked using the Health Canada smoking regime; per cigarette 15 puffs with a volume of 55 mL and a puff interval of 30 s is collected. The smoke of three cigarettes is accumulated on a glass fibre filter (Cambridge pad). Per cigarette type fifteen cigarettes are smoked. The pads are immediately extracted by shaking in Tris-HCl buffer (30 mL; pH 7.5; with internal standards NNK-d4 and NNN-d4 at 100 ng/mL). The extracts are then analysed for NNK, NNN and nicotine.

The bound NNK content in wBS is 7082 ng/g; the bound NNK content in aBS is 1594 ng/g; and the nicotine level in Burley cut-filler is 29.2 mg/g.

In the Burley blend without 20% wBS or 20% aBS, nicotine is 5 mg/cigarette, NNK is 245 ng/cigarette and NNN is 129 ng/cigarette.

In the Burley blend with 20% wBS, nicotine is 4 mg/cigarette, NNK is 701 ng/cigarette and NNN is 118 ng/cig.

In the Burley blend with 20% aBS, nicotine is 5 mg/cigarette, NNK is 390 ng/cigarette and NNN is 112 ng/cig.

A significant increase in NNK levels is found in the smoke of cigarettes with added washed Burley stems (wBS). In addition, the smoke NNK levels of cigarettes with aBS is significantly lower than the cigarettes with wBS. No significant reduction is observed for NNN or nicotine. This shows that the same matrix-bound NNK which is released upon autoclaving is also transferred to the aerosol during smoking. Interestingly, the cigarettes with aBS delivered significantly more smoke NNK than the pure Burley cigarettes. Without wishing to be bound by any theory, this indicates that a fraction of matrix-bound NNK is not released by the autoclaving method. From the difference in smoke-NNK of wBS and aBS cigarettes and the bound-NNK content of wBS (measured by autoclave extraction) the smoke transfer yield of bound-NNK (for this specific cigarette design and smoking regime) can be calculated as 30%. Since this transfer yield is very similar to that of nicotine (26%), it can be concluded that the release from the matrix-bound state is no significant hindrance to the smoke delivery of bound NNK. This means that bound NNK contributes in a similar way to smoke NNK concentrations as unbound "free" preformed NNK.

Example 8

Heat Release of NNK from Washed Burley Stem

Portions of washed Burley stem powder are inserted in the tips of Pasteur pipettes between plugs of glass wool. Thus, any NNK that evaporates during heating condenses at the colder parts of the pipette and can be extracted from the glass surface.

Either powdered washed Burley stem or washed Burley stem submitted to an additional autoclaving & washing is placed in the tips of Pasteur pipettes between plugs of glass wool. These samples are heated for 35 s at the nozzle of a heat gun. Subsequently, the part of the pipettes containing the sample or condensate are crushed and the glass hard, glass wool and tobacco powder are extracted together by shaking for 1 hour at room temperature in Tris-HCl buffer (5 ml; 50 mM; pH7.5; with internal standards: NNK-d4 and NNN-d4@100 ng/mL). Aliquots of the extracts are filtered and free NNK, NNN and nicotine are determined by LC-MS. The remaining extraction mixtures are heated in an autoclave (130° C. for 4 hours). Total NNK is determined by measuring the NNK content of the autoclaved extraction mixtures. The actual temperatures reached in this experimental setup are measured by placing a thermocouple in a tip of a Pasteur pipette filled with glass wool. The time-dependent temperature measurements showed that T-10° C. was reached after ~20 s.

Figure 5:
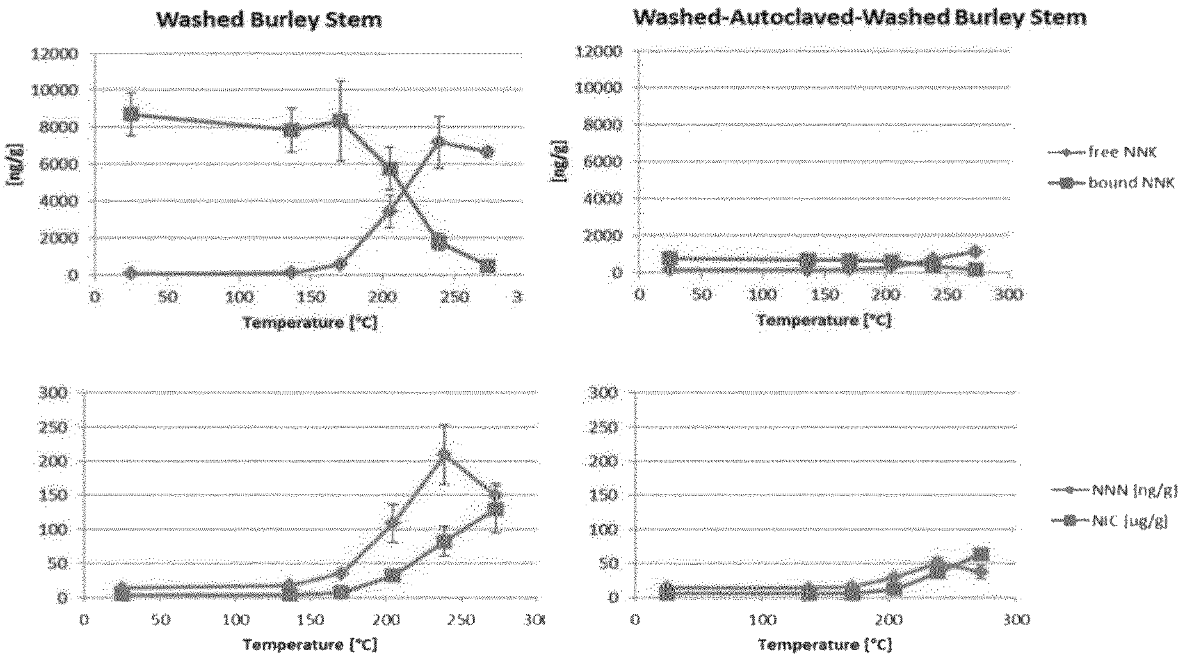
FIG. 5 shows the release of NNK, NNN and nictotine from washed Burley stem or washed-autoclaved-washed Burley stem at increasing temperature as determined using a thermocouple in a tip of a Pasteur pipette filled with glass wool and the tobacco material under test.

The results are presented in FIG. 5. A release of bound NNK to its free form is observed at temperatures above 200° C. Heating to a target temperature of 270° C. for 40 s—which means that the sample is above 260° C. for ~20 s—leads to an almost complete liberation of bound NNK. At this temperature a small fraction of the NNK (~20%) is degraded. The material from which ~90% of the bound NNK is removed by autoclaving and water-washing shows no release or formation of free NNK beyond the concentrations expected from the residual bound NNK concentrations. A release of nicotine and NNN is also observed starting at 200° C., but with much lower concentrations when compared to the content in the original Burley stem shreds (nicotine: 8.2 mg/g; NNN: 13 μg/g; free NNK: 2.9 μg/g). The observed NNK release temperatures of 200-250° C. suggest that matrix-bound NNK can contribute to smoke NNK in both, conventional cigarettes and new smoking devices in which tobacco is heated by external heat sources.

Any publication cited or described herein provides relevant information disclosed prior to the filing date of the present application. Statements herein are not to be construed as an admission that the inventors are not entitled to antedate such disclosures. All publications mentioned in the above specification are herein incorporated by reference. Various modifications and variations of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in cellular, molecular and plant biology or related fields are intended to be within the scope of the following claims.

TABLE 1

| Sample process | Free NNK [ng/g] | Bound NNK [ng/g] | NNN [ng/g] | Nicotine [mg/g] |
|---|---|---|---|---|
| wash/(110° C./10 minutes)/wash | 792 | 3209 | 1297 | 1.09 |
| wash/(130° C./30 minutes)/wash | 1543 | 1386 | 1253 | 1.21 |
| wash/(130° C./1 hour)/wash | 1859 | 809 | 1329 | 1.11 |
| wash/(120° C./1 hour)/wash | 1397 | 1520 | 1413 | 1.15 |
| wash/(110° C./1 hour)/wash | 934 | 2481 | 1496 | 1.16 |
| wash/no heating/wash | 716 | 4848 | 1394 | 1.28 |
| untreated stems | 965 | 2715 | 6658 | 6.73 |

The invention claimed is:

1. A method of reducing the amount of at least matrix-bound NNK in tobacco material comprising the steps of:

(a) providing tobacco material comprising at least matrix-bound NNK;

(b) measuring the level of at least matrix-bound NNK in the tobacco material of step (a);

(c) heating the tobacco material of step (a) for at least 30 seconds to a temperature of greater than 115 degrees Celsius in the presence of a liquid or steam to release at least a portion of the matrix-bound NNK from the insoluble tobacco matrix of the tobacco material;

(d) measuring the level of at least matrix-bound NNK in the tobacco material following step (c);

(e) comparing the levels of matrix-bound NNK obtained in steps (b) and (d) to determine whether at least matrix-bound NNK has been released from the tobacco material by step (d) compared to the tobacco material of step (a) as measured in step (b).

2. The method according to claim 1, wherein the tobacco material provided in step (a) is contacted with a first aqueous solution or solvent prior to step (c).

3. A method of reducing the amount of at least matrix-bound NNK in tobacco material comprising the steps of:

(a) providing tobacco material comprising at least matrix-bound NNK;

(b) measuring the level of at least matrix-bound NNK in the tobacco material of step (a);

(c) contacting the tobacco material of step (a) comprising at least one matrix-bound NNK with a first aqueous solution or solvent;

(d) heating the tobacco material of step (c) for at least 30 seconds to a temperature of greater than 115 degrees Celsius in the presence of a liquid or steam to release at least a portion of the matrix-bound NNK from the insoluble tobacco matrix of the tobacco material;

(e) measuring the level of at least matrix-bound NNK in the tobacco material following step (c);

(f) comparing the levels of matrix-bound NNK obtained in steps (b) and (d) to determine whether at least matrix-bound NNK has been released from the tobacco material of step (e) compared to the tobacco material of steps (a) as measured in step (b); and (g) removing the matrix-bound NNK from the tobacco material of step (e) by one or more washes with a second aqueous solution or solvent.

4. The method according to claim 3, wherein the first and second aqueous solutions or solvents are the same or different.

5. The method according to claim 1, wherein the tobacco material of step (a) is selected from the group consisting of: tobacco leaf and/or tobacco stems and/or tobacco dust and/or tobacco leaf prime lamina strip or a combination of two or more thereof.

6. The method according to claim 1 wherein the tobacco material of step (a) is heated in the presence of water or steam produced from water in step (c).

7. The method according to claim 1, wherein the tobacco material of step (a) is heated in step (c) in the presence of pressurised steam and/or superheated steam.

8. Tobacco material obtained or obtainable by the method of claim 1.

9. The method according to claim 1, wherein the tobacco material of step (a) is heated for at least 30 seconds to a temperature of greater than 120 degrees Celsius in the presence of a liquid or steam to release at least a portion of the matrix-bound NNK from the insoluble tobacco matrix of the tobacco material in step (c).

10. The method according to claim 1, wherein the tobacco material of step (a) is heated for at least 30 seconds to a temperature of greater than 125 degrees Celsius in the presence of a liquid or steam to release at least a portion of the matrix-bound NNK from the insoluble tobacco matrix of the tobacco material in step (c).

11. The method according to claim 1, wherein the tobacco material of step (a) is heated for at least 30 seconds to a temperature of greater than 130 degrees Celsius in the presence of a liquid or steam to release at least a portion of the matrix-bound NNK from the insoluble tobacco matrix of the tobacco material in step (c).

12. The method according to claim 1, wherein the tobacco material of step (a) is heated for at least 30 seconds to a temperature of greater than 135 degrees Celsius in the presence of a liquid or steam to release at least a portion of the matrix-bound NNK from the insoluble tobacco matrix of the tobacco material in step (c).

13. The method according to claim 1, wherein the tobacco material of step (a) is heated for at least 30 seconds to a temperature of greater than 140 degrees Celsius in the presence of a liquid or steam to release at least a portion of the matrix-bound NNK from the insoluble tobacco matrix of the tobacco material in step (c).

* * * * *